United States Patent
Anderson et al.

(10) Patent No.: US 10,899,865 B2
(45) Date of Patent: *Jan. 26, 2021

(54) BISPHENOL M DIPHTHALONITRILE ETHER RESIN BLENDS INCLUDING A FILLER, AND ARTICLES

(71) Applicant: 3M INNOVATIVE PROPERTIES COMPANY, St. Paul, MN (US)

(72) Inventors: Benjamin J. Anderson, Eden Prairie, MN (US); Jay R. Lomeda, St. Paul, MN (US); Wendy L. Thompson, Roseville, MN (US); Jeremy M. Higgins, Roseville, MN (US); Amit J. Patel, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 262 days.

This patent is subject to a terminal disclaimer.

(21) Appl. No.: 16/088,876

(22) PCT Filed: Mar. 31, 2017

(86) PCT No.: PCT/US2017/025233
§ 371 (c)(1),
(2) Date: Sep. 27, 2018

(87) PCT Pub. No.: WO2017/173195
PCT Pub. Date: Oct. 5, 2017

(65) Prior Publication Data
US 2020/0299506 A1 Sep. 24, 2020

Related U.S. Application Data

(60) Provisional application No. 62/316,248, filed on Mar. 31, 2016, provisional application No. 62/348,477, filed on Jun. 10, 2016, provisional application No. 62/475,396, filed on Mar. 23, 2017.

(51) Int. Cl.
| | | |
|---|---|---|
| *C08G 16/02* | (2006.01) | |
| *C08L 71/00* | (2006.01) | |
| *C08G 73/00* | (2006.01) | |
| *C07C 255/54* | (2006.01) | |
| *C07C 323/32* | (2006.01) | |
| *C08L 61/00* | (2006.01) | |

(52) U.S. Cl.
CPC ........ *C08G 16/0231* (2013.01); *C07C 255/54* (2013.01); *C07C 323/32* (2013.01); *C08G 73/00* (2013.01); *C08L 61/00* (2013.01); *C08L 71/00* (2013.01); *C08L 2205/025* (2013.01); *C08L 2205/035* (2013.01)

(58) Field of Classification Search
CPC .................................................... C08L 71/00
See application file for complete search history.

(56) References Cited

U.S. PATENT DOCUMENTS

| | | | |
|---|---|---|---|
| 3,429,722 A | 2/1969 | Economy | |
| 3,496,250 A | 2/1970 | Czerwinski | |
| 3,956,320 A | 5/1976 | Heath | |
| 4,223,123 A | 9/1980 | Keller | |
| 4,304,896 A | 12/1981 | Keller | |
| 4,408,035 A | 10/1983 | Keller | |
| 4,587,325 A | 5/1986 | Keller | |
| 4,764,578 A | 8/1988 | Malinge | |
| 5,003,039 A | 3/1991 | Keller | |
| 5,262,514 A * | 11/1993 | Keller | .......... C08G 73/10 528/220 |
| 5,312,887 A | 5/1994 | Papathomas | |
| 5,780,154 A | 7/1998 | Okano | |
| 6,297,298 B1 | 10/2001 | Keller | |
| 8,921,510 B1 | 12/2014 | Keller | |
| 9,221,970 B2 | 12/2015 | Schultz | |
| 2012/0214948 A1* | 8/2012 | Condo | ............ C08J 3/203 525/242 |
| 2012/0245253 A1 | 9/2012 | Schultz | |
| 2014/0275472 A1 | 9/2014 | Keller | |

FOREIGN PATENT DOCUMENTS

| | | |
|---|---|---|
| CN | 101395201 | 3/2009 |
| CN | 101831173 | 9/2010 |
| CN | 102086168 | 6/2011 |
| CN | 102887999 | 1/2013 |
| CN | 102936340 | 2/2013 |

(Continued)

OTHER PUBLICATIONS

Canlica, "Synthesis, characterization and electrochemical, and electrical measurements of novel 4,4'-1isopropylidendioxydiphenyl bridged bis and cofacial bis-metallophthalocyanines (Zn.Co)," Polyhedron, 2008, vol. 27, No. 7, pp. 1883-1890, XP022627496.

Derradji, "Effect of silane surface modified titania nanoparticles on the thermal, mechanical, and corrosion protective properties of a bisphenol-A based phthalonitrile resin," Progress in Organic Coatings, 2016, vol. 90, pp. 34-43.

Derradji, "High performance ceramic-based phthalonitrile micro and nanocomposites," Materials Letters, 2016, vol. 182, pp. 380-385.

Derradji, "New oligomeric containing aliphatic moiety phthalonitrile resins: their mechanical and thermal properties in presence of silane surface-modified zirconia nanoparticles," Iranian Polymer Journal, 2016, vol. 25, No. 6, pp. 503-514.

(Continued)

*Primary Examiner* — Vickey Nerangis
(74) *Attorney, Agent, or Firm* — Adrian L. Pishko

(57) ABSTRACT

The present disclosure provides a resin blend containing a blend of a first phthalonitrile resin, a filler, and a bisphenol M diphthalonitrile ether resin. Suitable fillers include at least one of nanoparticles, microparticles, or fibers. The present disclosure also provides an article including a polymerization product of such a resin blend. The resin blends can be prepared at lower temperatures than phthalonitrile resin blends without a bisphenol M diphthalonitrile ether resin.

15 Claims, 4 Drawing Sheets

(56) References Cited

FOREIGN PATENT DOCUMENTS

| CN | 102936466 | 2/2013 |
|---|---|---|
| CN | 103012790 | 4/2013 |
| CN | 105348734 | 2/2016 |
| JP | 62-149723 | 7/1987 |
| JP | 2008-530309 | 8/2008 |
| WO | WO 2006/086758 | 8/2006 |
| WO | WO 2011-050121 | 4/2011 |
| WO | WO 2014-051523 | 4/2014 |
| WO | WO 2017-172515 | 10/2017 |
| WO | WO 2017-173040 | 10/2017 |

OTHER PUBLICATIONS

Derradji, "Thermal and Mechanical Properties Enhancements Obtained by Reinforcing a Bisphenol-A Based Phthalonitrile Resin With Silane Surface-Modified Alumina Nanoparticles," Polymer Composites, 2017, pp. 1549-1558.
Dominguez, "Low-melting Phthalonitrile Oligomers: Preparation, Polymerization and Polymer Properties," High Performance Polymers, 2006, vol. 18, No. 3, pp. 283-304.
Dominguez, "Properties of phthalonitrile monomer blends and thermosetting phthalonitrile copolymers," Polymer, 2007, vol. 48, No. 1, pp. 91-97.
Hamciuc, "Poly(1,3,4-oxadiazole-ether-imide)s and their polydimethylsiloxane-containing copolymers," European Polymer Journal, 2007, vol. 43, No. 11, pp. 4739-4749, XP022318829.
Hamciuc, "Poly(ether-imide) and poly (ether-imide)-polydimethylsiloxane containing isopropylidene groups," Polymer Bulletin, 2008, vol. 59, pp. 825-832. XP019561586.
Hsiao, "Synthesis and Characterization of Polyimides Based on Isopropylidene-containing Bis(ether anhydride)s," Journal of Polymer Research, 1997, vol. 4, No. 3, pp. 183-190, XP019221958.
Keller, "High temperature resorcinol-based phthalonitrile polymer," Polymer, 2005, vol. 46, pp. 4614-4618.
Laskoski, "Improved Synthesis of Oligomeric Phthalonitriles and Studies Designed for Low Temperature Cure," Polymer Chemistry, 2014, vol. 52, pp. 1662-1668. XP055380215.
Laskoski, "Synthesis and Properties of a Bisphenol A Based Phthalonitrile Resin," Journal of Polymer Science, Part A: Polymer Chemistry, 2005, vol. 43, No. 18, pp. 4136-4143.
McKeown, "The Synthesis of Symmetrical Phthalocyanines," The Porphyrin Handbook, Phthalocyanines: Synthesis, 2003, vol. 15, pp. 61-124.
Sharman, "Synthesis of Phthalocyanine Precursors," The Porphyrin Handbook, Phthalocyanines: Synthesis, 2003, vol. 15, p. 1-60.
Takekoshi, "Synthesis of High Performance Aromatic Polymers via Nucleophilic Nitro Displacement Reaction," Polymer Journal, 1987, vol. 19, No. 1, pp. 191-202.
Zhou, "Study on One Phthalonitrile Resin System Suitable for RTM Process," ECCM15—15th European Conference on Composite Materials, Venice, Italy, Jun. 24-28, 2012, pp. 1-8.
International Search report for PCT International application No. PCT/US2017/24947 dated Jun. 21, 2017, 3 Pages.
International Search report for PCT International application No. PCT/US2017/024006 dated Jun. 6, 2017, 5 Pages.
International Search report for PCT International application No. PCT/US2017/025233, dated Jun. 19, 2017, 5 Pages.

* cited by examiner

BISPHENOL M DIPHTHALONITRILE ETHER RESIN BLENDS INCLUDING A FILLER, AND ARTICLES

CROSS REFERENCE TO RELATED APPLICATIONS

This application is a national stage filing under 35 U.S.C. 371 of PCT/US2017/025233, filed Mar. 31, 2017, which claims the benefit of U.S. Application No. 62/316,248, filed Mar. 31, 2016, U.S. Application No. 62/348,477, filed Jun. 10, 2016, and U.S. Application No. 62/475,396, filed Mar. 23, 2017, the disclosures of which are incorporated by reference in their entirety herein.

FIELD

The present disclosure relates to resin blends containing a filler, including bisphenol M diphthalonitrile ether resins.

BACKGROUND

Temperature resistant polymer networks are critical for an increasing number of industrial market applications. Applications are diverse from building and construction, electronics packaging, energy and power generation, and transportation. As the environmental temperature of an application increases, the number of available materials able to meet requirements shrinks rapidly.

Phthalonitrile (PN) resins are a class of network forming resins that when polymerized supply excellent thermal stability and degradation resistance, yet commercialization of phthalonitrile resin technology and use is hindered by poor processing properties, high cost, and high temperature autoclave cures. Phthalonitrile resins have high melt temperatures due to the rigid structure of many phthalonitrile molecules which incorporate a large percentage of aromatic structures to maintain the thermal performance of the phthalonitrile polymerized network. The phthalonitrile moiety is also rigid and planar and has a tendency to crystallize. These molecular structure attributes contribute to the high melt temperature of multifunctional PN resins. The high cost of the resin is driven by resin synthesis which utilizes higher cost starting materials (similar to anhydride and imide resins) and multistep synthesis routes. A high glass transition temperature of the polymerized resin imparts excellent thermal stability at high service temperatures, but also contributes to the need for high temperature multistep autoclave cures under inert atmosphere to achieve near full conversion.

SUMMARY

Resin blends containing one or more fillers are described. The resin blends provide improved processing (i.e., lower melt temperature, wider processing temperature window) and polymer network formation (i.e., lower polymerization temperature, out-of-autoclave polymerization reaction, lower network glass transition temperature) of diphthalonitrile ether resins, including improved incorporation of fillers into the resin blends.

In a first aspect, a resin blend is provided. The resin blend comprises a blend of a first phthalonitrile resin, a filler, and a bisphenol M diphthalonitrile ether resin. The first phthalonitrile resin is not a bisphenol M diphthalonitrile ether resin.

In a second aspect, an article is provided. The article comprises a polymerization product of the resin blend of the first aspect. In certain embodiments, the bisphenol M diphthalonitrile ether resin is of Formula I:

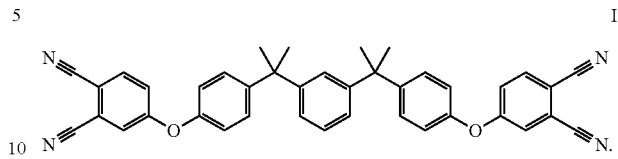

Temperature resistant polymer networks are critical for an increasing number of market applications. As the environmental temperature of an application increases, the number of available materials able to meet requirements shrinks rapidly. The present resin blends containing fillers are useful for applications in which a temperature resistant polymer is beneficial.

DETAILED DESCRIPTION

Figure 1:
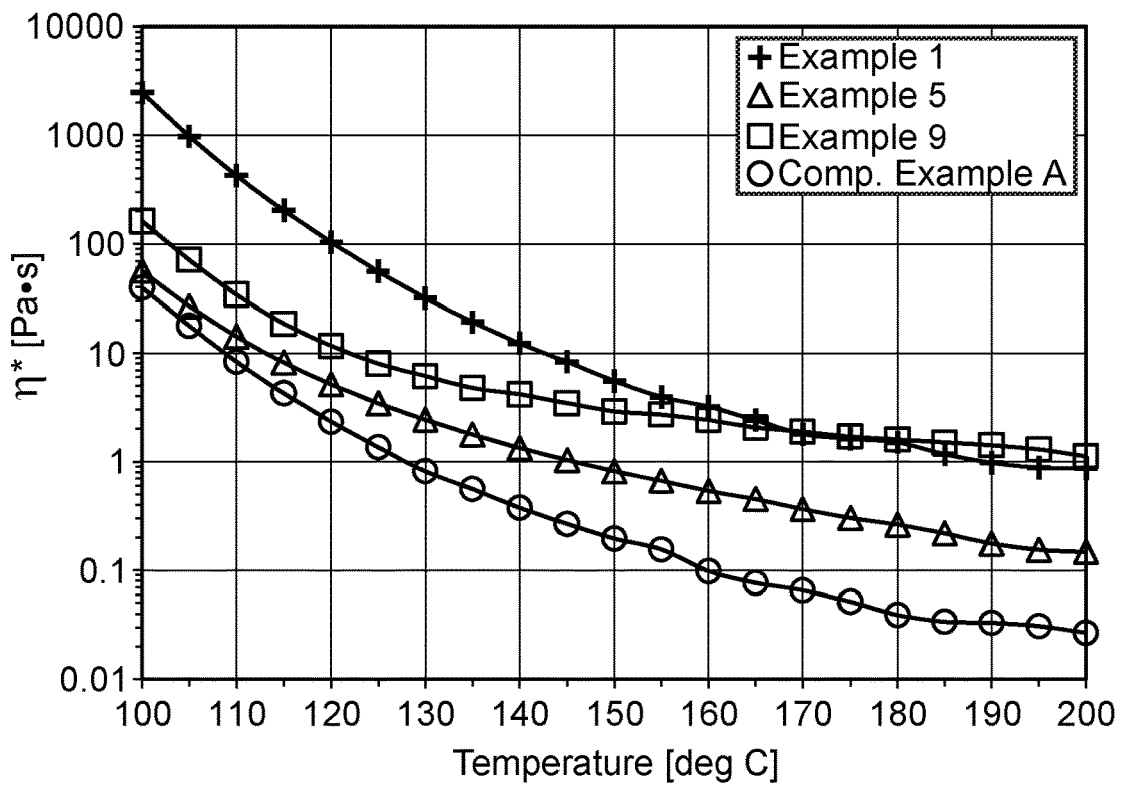
FIG. 1 is a graph of complex shear viscosity as a function of temperature of the filled resin blends of Example 1 (crosses), Example 5 (triangles), Example 9 (squares), and Comparative Example A (circles).

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

As used herein, the term "phthalonitrile" is inclusive of compounds having the characteristic benzene derivative having two adjacent nitrile groups. In the illustrated phthalonitrile group, R is for instance and without limitation, ether, thioether, aryl, alkyl, halogen, amine, ester, or amide, heteroalkyl, or (hetero)hydrocarbyl.

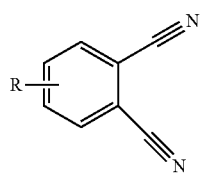

As used herein, "bisphenol M diphthalonitrile ether" refers to bis(3,4-dicyanophenyl) ether of bisphenol M.

As used herein, "bisphenol T diphthalonitrile ether" refers to bis(3,4-dicyanophenyl) ether of bisphenol T.

As used herein, "bisphenol P diphthalonitrile ether" refers to bis(3,4-dicyanophenyl) ether of bisphenol P.

As used herein, "resorcinol diphthalonitrile ether" refers to bis(3,4-dicyanophenyl) ether of resorcinol.

As used herein, a "particle" has an aspect ratio of less than 50:1 of the largest dimension to the smallest dimension, and excludes fibers. As used herein, "nanoparticle" refers to a particle having a D90 particle diameter below 1 micrometer (e.g., "submicron"). As used herein, "particle diameter" refers to the largest dimension of a particle. A suitable method to determine the particle diameter of a nanometer scale particle includes transmission electron microscopy (TEM). As used herein, "microparticle" refers to a particle having a D90 particle diameter below 1 millimeter. A suitable method to determine the particle diameter of a micrometer scale particle includes dynamic light scattering. As used herein, "D90" refers to 90 percent of a population of particles having a particle diameter below the particular particle diameter value.

As used herein, "nanofiller" refers to an additive included in a resin blend that has at least two dimensions (of height, width, and length) that are less than 1 micrometer. As used herein, "microfiller" refers to an additive included in a resin blend that has at least two dimensions (of height, width, and length) that are less than 1 millimeter.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, Si, P, and N, and both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to, methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of (hetero)hydrocarbyl alkyl and aryl groups, and hetero(hetero)hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero) hydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

As used herein, the term "polymerized product" refers to the result of a polymerization reaction of a polymerizable composition.

As used herein, the term "residue" is used to define the (hetero)hydrocarbyl portion of a group remaining after removal (or reaction) of the attached functional groups, or the attached groups in a depicted formula. For example, the "residue" of butyraldehyde, $C_4H_9$—CHO is the monovalent alkyl $C_4H_9$—. The residue of phenylene diamine $H_2N$—$C_6H_4$—$NH_2$, is the divalent aryl —$C_6H_4$—.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

The present disclosure is generally directed to resin blends and articles. In a first aspect, a resin blend is provided. The resin blend comprises a blend of a first phthalonitrile resin, a filler, and a bisphenol M diphthalonitrile ether resin. In a second aspect, an article is provided. The article comprises a polymerization product of the resin blend according to the first aspect.

Preferably, the article exhibits a glass transition temperature between 200 and 350 degrees Celsius. The present disclosure details processes for the dispersion of one or more fillers in liquid phthalonitrile monomer resins and the cure of the same into a (e.g., particle and/or fiber) filled polymer network. In certain embodiments, the disclosure details processes for the fabrication of fiber reinforced polymer network composite articles utilizing liquid phthalonitrile monomer resins and particle filled liquid phthalonitrile monomer resins. The phthalonitrile resins and filled phthalonitrile resins utilize a novel phthalonitrile monomer resin technology that offers liquid resins at temperatures less than 200 degrees Celsius, even less than 150 degrees Celsius, offering the ability to compound the phthalonitrile resin with particulates at temperatures below the characteristic polymerization temperature window of the polymer network formation reaction of the phthalonitrile monomer resins. Particle filled phthalonitrile polymerized networks were discovered to demonstrate greater stiffness and in some cases higher softening temperature, toughness and/or thermal conductivity, while maintaining other material properties such as strength and degradation resistance, when compared to the neat phthalonitrile cured polymer network. The low viscosity of the phthalonitrile resins and the particle filled phthalonitrile resins enable the resins to be better suited than previous phthalonitrile resin systems in the fabrication of fiber reinforced polymer composite articles.

Multifunctional phthalonitrile monomer resins are a class of network forming resins that when polymerized supply excellent thermal stability and degradation resistance. Phthalonitrile resins have high melt temperatures of near and in excess of 200 degrees Celsius due to the rigid structure of many phthalonitrile monomers, which incorporate a large percentage of aromatic structures to maintain the thermal performance of the phthalonitrile polymerized network. The phthalonitrile moiety is also rigid and planar and has a tendency to crystallize. These molecular structure attributes contribute to the high melt temperature of multifunctional phthalonitrile resins. The high cost of the resin is driven by resin synthesis, which utilizes high cost starting materials similar to anhydride and imide resins, plus multistep synthesis routes (Sharman, W. M. and J. E. Van Lier, *Synthesis of Phthalocyanine Precursors*, in *The Porphyrin Handbook*, K. M. Kadish, K. M. Smith, and R. Guilard, Editors. 2003, Academic Press: Amsterdam. p. 1-60).

Phthalonitriles undergo an addition polymerization reaction when promoted by a catalyst or curative. Known catalyst systems for phthalonitrile polymerization are the addition of a base and an alcohol and heat, the addition of a suitable reducing agent and heat, and the addition of metals or organometals or metal salts and heat (U.S. Pat. No. 4,304,896 to Keller et al.). Many metals have been shown to result in phthalonitrile polymerization (McKeown, N. B., *The Synthesis of Symmetrical Phthalocyanines*, in *The Porphyrin Handbook*, K. M. Kadish, K. M. Smith, and R. Guilard, Editors. 2003, Academic Press: Amsterdam. p. 61-124). In the absence of a primary alcohol, primary amines act as phthalonitrile curatives (U.S. Pat. No. 4,408,035 to Keller and U.S. Pat. No. 4,223,123 to Keller et al.). The catalyst or curative promoted phthalonitrile polymerization reaction proceeds at an appreciable rate between temperatures of 200 to 250 degrees Celsius. Amine cured phthalonitrile polymerized networks have demonstrated excellent thermal stability imparted by a high glass transition temperature, good thermal and thermo-oxidative degradation resistance, inherent non-flammability and low moisture uptake (Dominguez, D. D. and T. M. Keller, *Properties of phthalonitrile monomer blends and thermosetting phthalonitrile copolymers*. Polymer, 2007. 48(1): p. 91-97).

The compounding of phthalonitrile resins with (e.g., particulate or fiber) filler and the polymerization of said resin into a networked polymer has been difficult due to the physical and reactive properties of phthalonitrile resins. This has hindered development of specific property enhanced filled phthalonitrile polymerized networks. The melt temperature of phthalonitrile resins requires the filler compounding to proceed at temperatures in excess of 200 degrees Celsius in order to maintain a liquid resin melt with a manufacturing acceptable viscosity. High temperature compounding for phthalonitrile resins has been prohibitive, for instance, for many mineral fillers and filler surface modifying additives due to the activity of said fillers and additives to initiate network polymerization of the phthalonitrile. Hence, compounding phthalonitrile resins with mineral fillers such as metals and metal salts and surface modifying agents such as organoacids and organobases at temperatures over 200 degrees Celsius is problematic since many have catalytic activity to initiate phthalonitrile polymerization. The high compounding temperature is sufficient to readily promote phthalonitrile polymerization leading to an inability to process the filled resin due to increasing resin viscosity, shortening of resin working time, and solidification due to resin gelation. Therefore, the compounding of traditional phthalonitrile resins with fillers and/or other additives is challenging due to the high temperatures needed to melt and liquefy the monomer resins. These same high temperatures necessary to achieve a manufacturing acceptable viscosity and the short working time of the resin have limited the application of phthalonitrile resins and particle filled phthalonitrile resins as matrix resin systems in fiber reinforced polymer composites. Thus, the commercial implementation of phthalonitrile resins in fiber reinforced polymer composites is also intractable.

The structure of the BMPN appears to greatly suppress the melt temperature of the phthalonitrile when compared to bisphenol P diphthalonitrile (BPPN) and other phthalonitrile resins. The reduction in melt temperature is dramatic when comparing BMPN to BPPN. The BMPN and BPPN resins are isomers and differ in structure by the connectivity at the central phenyl ring, BMPN having meta connectivity on the central phenyl ring (see Formula I below) and BPPN having para connectivity on the central phenyl ring (see Formula II below). Unexpectedly, the difference in connectivity translates into a melt temperature of 160° C. for BMPN compared to 213° C. for BPPN. The melt temperature of BMPN is lower than other reported bisphenol phthalonitriles (Takekoshi, T., *Synthesis of High Performance Aromatic Polymers via Nucleophilic Nitro Displacement Reaction.* Polym J, 1987. 19(1): p. 191-202).

Interestingly, BMPN displays the ability to exist as a supercooled liquid at temperatures below its melt temperature, a property that has not been displayed by other bisphenol based phthalonitrile resins. This attribute adds a processing advantage to BMPN by enabling liquid resin processing at temperatures below the melt temperature, providing a larger delta T between the cure exotherm of the resin and the resin melt temperature. A larger delta T provides a greater processing window and longer gel times for a BMPN resin system (e.g., BMPN with a curative or catalyst added) compared to other phthalonitrile resin systems. This supercooled liquid property has been exemplified through monitoring the resin viscosity at a temperature, 135° C., below the resin melt temperature. The measurements demonstrated the slow crystallization time of the BMPN resin under different flow sampling conditions and the use of short duration low shear flow as a means of maintaining the supercooled liquid state.

Bisphenol M diphthalonitrile (BMPN) and BMPN based phthalonitrile resin blend technology enables melting phthalonitrile resins at temperatures below 200 degrees Celsius. The BMPN resin blend technology employs BMPN resin as a resin blend component, plus one or more additional phthalonitrile resins. The low melt temperature of 160 degrees Celsius and supercooled liquid behavior of BMPN enables the resin and resin blends to maintain a liquid state at temperatures well below 200 degrees Celsius, and even below the melt temperature of BMPN for extended periods of time. When BMPN is employed as a resin component in resin blends with other phthalonitrile resins, phthalonitrile blends can maintain a liquid viscosity down to a temperature as low as 50 to 60 degrees Celsius, near the glass transition temperature of the resin blend. It has been discovered that the ability of BMPN and BMPN based phthalonitrile resin blends to maintain a liquid viscosity at temperatures below 200 degrees Celsius enables the compounding of phthalonitrile resins with resin fillers and/or other additives, whereas previous compounding methods were either difficult or not possible with phthalonitrile monomer resins due to high melt temperatures and resin polymerization.

The present disclosure demonstrates the compounding of a BMPN based phthalonitrile blend with bare and surface modified particles (e.g., calcite, silica, silicon carbide, alumina, boron nitride, and glass bubbles) at temperatures below 200 degrees Celsius with no physical or thermal signs of cure initiation. The compounding techniques utilized include impellar mixing, high shear mixing, milling, centrifugal mixing, and solution dispersion of particles into the phthalonitrile monomer resin. The present disclosure further demonstrates the fabrication of a fiber reinforced polymer composite by resin impregnation using an unfilled BMPN based phthalonitrile resin blend system and a particle filled BMPN based phthalonitrile resin blend system. Resin impregnation of the fibers was performed at temperatures well below 200 degrees Celsius, where the resin system maintained a low viscosity and a long working time.

Cost has been a hindrance to phthalonitrile resins obtaining commercial relevance. The high cost of the phthalonitrile resin is traced to the cost of the precursor resin synthesis materials and a multistep synthesis scheme. The filled BMPN resin and resin blends of at least certain embodiments disclosed herein enable processable filled phthalonitrile resins that benefit from the cost advantage of low cost filler incorporation over previous phthalonitrile resins. Solution dispersion and stripping offers significant cost reduction compared to the resin material cost, while the mixing and milling of, e.g., calcite particles and the centrifugal mixing of other particles into the resin offers even greater opportunity for cost reduction.

As noted above, in a first aspect, a resin blend is provided comprising a blend of a first phthalonitrile resin, a filler, and a bisphenol M diphthalonitrile ether resin. In a second aspect, an article is provided comprising a polymerization product of the resin blend according to the first aspect.

In resin blends of the present disclosure, usually the bisphenol M diphthalonitrile ether resin is of Formula I:

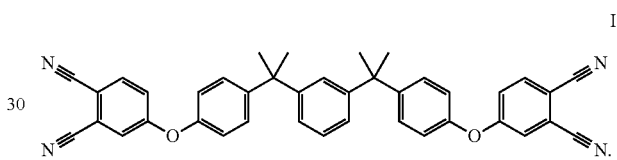

I

The monomer of Formula I may also be referred to as the bis(3,4-dicyanophenyl) ether of bisphenol M. A polymerized product of the monomer of Formula I typically exhibits a glass transition temperature between 200 to 250 degrees Celsius.

In select embodiments of resin blends according to the present disclosure, the first phthalonitrile resin is of Formula II, Formula III, Formula IV, or a combination thereof:

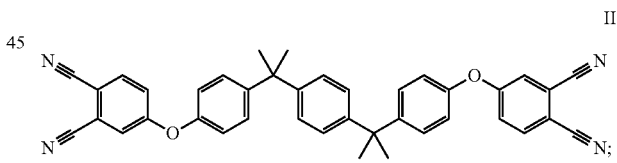

II

III

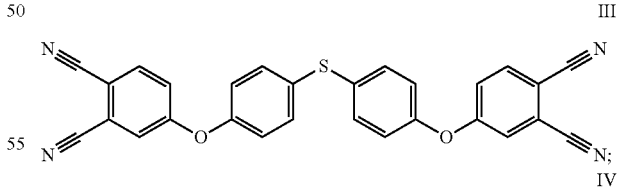

IV

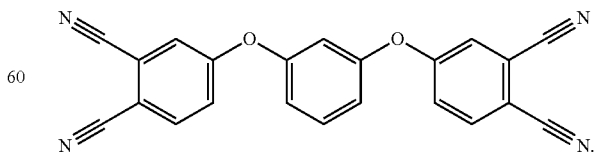

The monomer of Formula II may also be referred to as the bis(3,4-dicyanophenyl) ether of bisphenol P, or BPPN. A polymerized product of the monomer of Formula II typically exhibits a glass transition temperature of 250 to 300 degrees Celsius. The monomer of Formula III may also be referred to as the bis(3,4-dicyanophenyl) ether of bisphenol T, or BTPN. The monomer of Formula IV may also be referred to as the bis(3,4-dicyanophenyl) ether of resorcinol, or RPN. In certain embodiments, the first phthalonitrile resin comprises a bisphenol P diphthalonitrile ether resin of Formula II. In some embodiments, the first phthalonitrile resin comprises a bisphenol T diphthalonitrile ether resin of Formula III. In certain embodiments, the first phthalonitrile resin comprises a resorcinol diphthalonitrile ether resin of Formula IV.

The amounts of the two phthalonitrile resins is not particularly limited. In some embodiments, a weight ratio of the first phthalonitrile resin to the bisphenol M diphthalonitrile ether resin ranges from 10:90 to 90:10, inclusive; or from 15:85 to 85:15, inclusive; or from 30:70 to 70:30, inclusive. In select embodiments, the resin blend comprises a blend of each of the monomers of Formula I, Formula II, Formula III, and Formula IV.

In certain embodiments, resin blends according to the present disclosure further comprises at least one additional phthalonitrile resin. Example additional phthalonitrile resins include for instance and without limitation bis(3,4-dicyanophenyl) ether of bisphenol A, bis(2,3-dicyanophenyl) ether of bisphenol A, bis(3,4-dicyanophenyl) ether of bisphenol AP, bis(3,4-dicyanophenyl) ether of bisphenol AF, bis(3,4-dicyanophenyl) ether of bisphenol B, bis(3,4-dicyanophenyl) ether of bisphenol BP, bis(3,4-dicyanophenyl) ether of bisphenol C, bis(3,4-dicyanophenyl) ether of bisphenol C2, bis(3,4-dicyanophenyl) ether of bisphenol E, bis(3,4-dicyanophenyl) ether of bisphenol F, bis(3,4-dicyanophenyl) ether of 3,3',5,5'-tetramethylbisphenol F, bis(3,4-dicyanophenyl) ether of bisphenol FL, bis(3,4-dicyanophenyl) ether of bisphenol G, bis(3,4-dicyanophenyl) ether of bisphenol S, bis(3,4-dicyanophenyl) ether of bisphenol P, bis(3,4-dicyanophenyl) ether of bisphenol PH, bis(3,4-dicyanophenyl) ether of bisphenol TMC, bis(3,4-dicyanophenyl) ether of bisphenol Z, bis(3,4-dicyanophenyl) ether of 4,4'-dihydroxybiphenyl, bis(3,4-dicyanophenyl) ether of 4,4'-dihydroxydiphenyl ether, bis(3,4-dicyanophenyl) ether of catechol, bis(3,4-dicyanophenyl) ether of 4,4'-dihydroxybenzophenone, 3,4-dicyanophenyl ether of phenol, 2,3-dicyanophenyl ether of phenol, 4-tert-butylphthalonitrile, 4-butoxyphthalonitrile, 3,4-dicyanophenyl ether of 4-cumylphenol, 3,4-dicyanophenyl ether of 2-allylphenol, 3,4-dicyanophenyl ether of eugenol. Typically the resin blend (of two or more resins) is a solid at 25° C.

Synthesis of BMPN, BPPN, and BTPN can be achieved by the nucleophilic substitution of the nitro group of 4-nitrophthalonitrile by phenolic residues of the bisphenols catalyzed by potassium carbonate in DMSO. The reactions can be conducted at ambient temperature under a nitrogen atmosphere.

A method of making a polymerized network typically includes obtaining a monomer of Formula I; blending the monomer with at least one more phthalonitrile resin, a curative, a catalyst (e.g., a base such as 1,5-diazabicyclo (4.3.0)non-5-ene or 1,8-diazabicyclo[5.4.0]undec-7-ene; reducing agents such as hydroquinone and 1,2,3,6-tetrahydropyridine; metal, organometals or metal salts such as copper, iron, copper acetylacetonate, zinc naphthenate, dibutyltin dilaurate, stannous chloride, stannic chloride, copper chloride, iron chloride, and/or calcium carbonate), or a combination thereof to form a monomer blend (or resin blend); and subjecting the monomer blend to a temperature of no more than 300 degrees Celsius to form a fully polymerized network. Generally, the composition is heated to a temperature between about 50° C. and 300° C., such as between about 130-300° C., for a time of about 1-480 minutes. Suitable sources of heat include induction heating coils, ovens, hot plates, heat guns, infrared sources including lasers, microwave sources.

Solvents can be used as a processing aid. Useful solvents are ketones such as acetone, methyl ethyl ketone, methyl isobutyl ketone, cyclopentanone and cyclohexanone; amides such as acetamide, formamide, N,N-dimethylforamide, N-methylpyrrolidinone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl)ethanol, 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, methyl cellosolve acetate, methyl formate; and other solvents such as tetrahydrofuran, methylene chloride, dichloromethane, chloroform, acetonitrile, nitromethane, glycol sulfite and 1,2-dimethoxyethane (glyme).

In some embodiments of the method the monomer blend is subjected to a temperature of no more than 300 degrees Celsius in air. Optionally, the monomer blend is subjected to a temperature of no more than 300 degrees Celsius at ambient pressure.

The filler to be included in the resin blends according to the present disclosure is not particularly limited, and may include nanoparticles, microparticles, discontinuous fibers, continuous fibers, and combinations thereof. In certain embodiments, the filler comprises a nanofiller comprising metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof. Optionally, the filler comprises a nanofiller comprising calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof. As used herein, the term "nano" or "micro" in front of a material is interchangeable with reference of that material as a nanoparticle or microparticle, respectively (e.g., "nanosilica" is interchangeable with "silica nanoparticles", "microcalcite" is interchangeable with "calcite microparticles", etc.). For instance and without limitation, some suitable nanoparticles include silica nanoparticles available from Nalco Company (Naperville, Ill.) under the trade designation NALCO 15827; and silicon carbide nanoparticles available from 3M Technical Ceramics (Kempten, Germany) under the trade designation VSN1393.

Typically, a nanofiller is present in resin blends according to the present disclosure in an amount of 1 weight percent or more, 3 weight percent or more, 5 weight percent or more, 8 weight percent or more, 10 weight percent or more, 12 weight percent or more, 15 weight percent or more, 20 weight percent or more, or even 25 weight percent or more, based on the total weight of the resin blend; and 40 weight percent or less, 38 weight percent or less, 36 weight percent or less, 34 weight percent or less, 32 weight percent or less, 30 weight percent or less, 28 weight percent or less, 26 weight percent or less, 24 weight percent or less, 22 weight percent or less, 20 weight percent or less, 18 weight percent or less, or 15 weight percent or less, based on the total weight of the resin blend. Stated another way, a nanofiller may be present in a resin blend in an amount of 1 to 40 weight percent, 1 to 20 weight percent, 3 to 15 weight percent, 20 to 40 weight percent, or 25 to 40 weight percent, based on the total weight of the resin blend.

In certain embodiments, the filler comprises a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof. Optionally, the filler comprises a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof. For instance and without limitation, some suitable microparticles include boron nitrile microparticles available from 3M Company (St. Paul, Minn.) under the trade designation 3M BORON NITRIDE COOLING FILLER PLATELETS; glass bubbles available from 3M Company (St. Paul, Minn.) under the trade designation 3M GLASS BUBBLES IM16K; and alumina microparticles available from Micron Corp (a subsidiary of the Nippon Steel and Sumikin Materials Co., Japan) under the trade designation MICRON TA6Y1 ALUMINA.

Typically, a microfiller is present in resin blends according to the present disclosure in an amount of 1 weight percent or more, 5 weight percent or more, 10 weight percent or more, 15 weight percent or more, 20 weight percent or more, 30 weight percent or more, 40 weight percent or more, 50 weight percent or more, or even 60 weight percent or more, based on the total weight of the resin blend; and 90 weight percent or less, 85 weight percent or less, 80 weight percent or less, 75 weight percent or less, 70 weight percent or less, 65 weight percent or less, 55 weight percent or less, 45 weight percent or less, 35 weight percent or less, or 25 weight percent or less, based on the total weight of the resin blend. Stated another way, a nanofiller may be present in a resin blend in an amount of 1 to 90 weight percent, 1 to 50 weight percent, 5 to 35 weight percent, 20 to 55 weight percent, or 60 to 90 weight percent, based on the total weight of the resin blend.

Generally, the optional surface modifiers of the present disclosure include at least a binding group and a compatibilizing segment. The compatiblizing segment is selected to improve the compatibility of filler with the curable resin. Generally, the selection of the compatibilizing group depends on a number of factors including the nature of the curable resin, the concentration of the filler, and the desired degree of compatibility. Useful compatibilizing groups include for instance and without limitation, polyalkylene oxide residues (e.g., polypropylene oxide, polyethylene oxide, and combinations thereof), aromatic residues (e.g. phenyl, phenylalkylene, substituted phenylene, and combinations thereof, carbonyl residues (e.g., ketone, ester, amide, carbamate, and combinations thereof). The binding group bonds to the particle surface, connecting the surface-modifying agent to the filler. In the case of calcite particles, unlike many silica-based nanoparticle systems wherein the surface-modifying agents are covalently bonded to the silica, the surface-modifying agents of the present disclosure are ionically bonded to or physically bonded to (e.g., associated with) the calcite particles. Depending on the filler surface and the surface modifier, the surface modifier may be one or more of covalently bonded, ionically bonded, or physically bonded to a surface of the filler.

Some suitable surface modifiers comprise an organoacid, an organobase, a siloxane, a silane, or a combination thereof. The type of surface modifier will depend on the material of the filler. For instance, the surface modifier may comprise a silane or a siloxane when the filler comprises silica nanoparticles, silica microparticles, cenospheres, zirconia nanoparticles, zirconia microparticles, magnesium oxide nanoparticles, magnesium oxide microparticles, silicon carbide nanoparticles, silicon carbide microparticles, or a combination thereof. The surface modifier may comprise an organoacid or an organobase when the filler comprises calcite nanoparticles, calcite microparticles, magnesium oxide nanoparticles, magnesium oxide microparticles, alumina nanoparticles, alumina microparticles, dolomite nanoparticles, dolomite microparticles, boehmite nanoparticles, boehmite microparticles, or a combination thereof. The surface modifier may comprise an organoacid when the filler comprises zirconia nanoparticles, zirconia microparticles, magnesium oxide nanoparticles, magnesium oxide microparticles, or a combination thereof. The surface modifier may comprise an organosulfonate and/or an organophosphate when the filler comprises calcite nanoparticles, calcite microparticles, or a combination thereof. For example, the sulfonate and phosphate ends of organosulfonates and organophosphates, respectively, associate with the calcite surface by the formation of an ionic complex between sulfonate and phosphate of the surface modifier and calcium of the calcite. The organic end of the surface modifier stabilizes the calcite in the phthalonitrile resin, resulting in a calcite dispersion in the liquid resin melt and stabilized calcite in the cured polymer network. At least certain embodiments of the present disclosure utilize polypropylene oxide and polyethylene oxide as the organic end of any of the surface modifiers described herein, associated with the monomer resin and polymer network.

For instance, according to the present disclosure, calcite and a surface modifier were impeller mixed and milled into the phthalonitrile resin. The surface modifier absorbs to the calcite surface and stabilizes the calcite in the resin. Alumina, boron nitride, and glass bubbles were centrifugally mixed into the phthalonitrile resin. Silica and silicon carbide, in contrast, were surface modified with phenyltrimethoxyoxysilane, which was hydrolyzed in a water/alcohol sol of the silica and silicon carbide and condensed with reactive surface silanols on the particle surface. Particle sols were blended with the phthalonitrile resin and solvent stripped. The phenyl modified surface compatibilizes the silica nanoparticles and silicon carbide nanoparticles in the phthalonitrile resin. The filled resins maintain a working time comparable to the unfilled resin when a curative or catalyst is added.

Impeller mixing and milling as a compounding technique for calcite filled BMPN phthalonitrile resin or resin blends provides process simplicity, ease, and low cost compared to other compounding techniques. Impellar mixing disperses the calcite in the resin and breaks the particle size down to micrometer particle diameters. Milling as a follow-on process breaks the calcite down to nanometer particle diameters, while the surface modifier stabilizes the calcite in the resin. Impellar mixing plus milling enables the low cost of the filler to be effectively transferred to the cost of the filled resin. The BMPN resin and BMPN based phthalonitrile blends enable mixing and milling as compounding techniques where previous phthalonitrile resins do not, by maintaining a liquid state at temperatures well below 200 degrees Celsius.

At temperatures near to 60 degrees Celsius, solvent is often added to reduce the viscosity of the resin. Some suitable solvents miscible with phthalonitrile resins include methyl ethyl ketone (MEK), methyl isobutyl ketone (MIBK), diacetone alcohol, dimethylformamide (DMF), and dimethyl sulfoxide (DMSO). At higher temperatures (e.g., greater than 120 degrees Celsius but less than 200 degrees Celsius), mixing and milling can be performed without the addition of solvent in a liquid resin melt. An advantage of high temperature mixing and milling is the removal of solvent stripping.

A surface modifying agent for a filler surface is selected such that one end of the surface modifier preferentially associates with the filler surface and the other end of the surface modifier preferentially associates with the monomer resin and maintains particle compatibility in the resin and polymerized network. The concentration of a surface modifier can be tuned to minimize free surface modifier in the resin and avoid open filler (e.g., calcite) surface, both of which would catalyze phthalonitrile polymerization over 200 degrees Celsius.

In certain embodiments, the filler comprises at least one of reinforcing continuous fibers or reinforcing discontinuous fibers. Exemplary fibers include carbon (e.g., graphite) fibers, glass fibers, ceramic fibers, boron fibers, silicon carbide fibers, polypropylene fibers, polyacrylonitrile fibers, polyimide fibers, polyamide fibers, and polyethylene fibers. Combinations of materials may also be used. Generally, the form of the fibers is not particularly limited. Exemplary continuous fiber forms include unidirectional arrays of individual continuous fibers, yarn, roving, braided, and nonwoven mats. Discontinuous fibers are not particularly limited, and for example include inorganic fibers, such as glass, alumina, aluminosilicate, carbon, basalt, or a combination thereof. The discontinuous fibers typically have an average length of less than 5 centimeters.

Discontinuous fibers may be formed from continuous fibers, for example, by methods known in the art such as chopping, shearing, and milling. Typically, the plurality of discontinuous fibers comprises an aspect ratio of 10:1 or greater.

Suitable discontinuous fibers can have a variety of compositions, such as ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serve as aids in textile processing. The sizing can be removed from the ceramic filaments by heat cleaning the filaments or ceramic fibers as a temperature of 700° C. for one to four hours. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers which contain less than about 2% alkali or are substantially free of alkali (i.e., "E-glass" fibers). E-glass fibers are available from numerous commercial suppliers.

The ceramic fibers can be cut or chopped so as to provide relatively uniform lengths, which can be accomplished by cutting continuous filaments of the ceramic material in a mechanical shearing operation or laser cutting operation, among other cutting operations. Given the highly controlled nature of such cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

The amount of discontinuous fibers dispersed in the resin blend is not particularly limited. The plurality of fibers is often present in an amount of at least 1 weight percent of the resin blend, at least 2 weight percent, at least 3 weight percent, at least 5 weight percent, at least 10 weight percent, at least 15 weight percent, at least 20 weight percent, or at least 25 weight percent of the resin blend; and up to 50 weight percent, up to 45 weight percent, up to 40 weight percent, or up to 35 weight percent of the resin blend. In certain embodiments, the fibers are present in the resin blend in an amount of between 1 weight percent and 50 weight percent, or between 2 weight percent and 25 weight percent, or between 5 weight percent and 15 weight percent, inclusive, of the resin blend. In certain embodiments, discontinuous fibers are present in an amount of between 5 weight percent and 50 weight percent, inclusive, of the resin blend.

For example, a calcite filled BMPN based resin system produced by impeller mixing of calcite and a surface modifier, and followed by milling of the calcite to dimensions of less than 400 nm, has been employed in the fabrication of a fiber reinforced polymer composite. The nanometer dimension of the particles enables penetration of the resin and particle into the fiber bundles (without filtering of the particles). The low viscosity of the BMPN based resin system enables impregnation of the fiber at temperatures well below 200 degrees Celsius. The present disclosure also describes resin transfer molding as a manufacturing method for liquid phthalonitrile resin impregnation of fiber in the production of a fiber reinforced polymer composite. Other in-line liquid resin impregnation methods of fibers enabled by the BMPN based resin include pultrusion and filament winding. A fiber reinforced polymer composite has also been demonstrated with an unfilled BMPN based resin system using a resin transfer molding process similar to the process employed for the calcite filled phthalonitrile resin system.

Solution dispersion followed by solvent stripping can be a preferred method for the introduction of silica and silicon carbide into the BMPN phthalonitrile and phthalonitrile resin blends. The solution dispersion method for silica and silicon carbide is low cost compared to the expense of the phthalonitrile resin and yields well dispersed particles in the liquid resin melt at temperatures below 200 degrees Celsius. For example, the silica and silicon carbide were each surface modified with phenyltrimethoxysilane in a water/alcohol suspension and transferred to a solvent (e.g. methoxypropanol, acetone, MEK, MIBK, tetrahydrofuran (THF), dichloromethane, diacetone alcohol, DMF, DMSO) miscible with phthalonitrile resins. The particle sol was added at elevated temperature (e.g., greater than 120 degrees Celsius) to the undiluted phthalonitrile resin where the resin is a low viscosity liquid resin melt. The particle sol can be added at lower temperatures (e.g., less than 120 degrees Celsius) to the phthalonitrile resin diluted with a miscible solvent to lower the resin viscosity. Solvent is stripped from the particle filled resin at temperatures less than 200 degrees Celsius, where the BMPN phthalonitrile resin or resin blend remains in a liquid melt state. The phenyl treated surface of the particle stabilizes the particles in the liquid resin melt and in the cured polymer network.

Centrifugal mixing of alumina, boron nitride, glass bubbles and silane surface modified glass bubbles offers a short time and efficient means of particle dispersion in the BMPN phthalonitrile and phthalonitrile resin blends. Particles are dispersed in the liquid resin at a temperature below 200 degrees Celsius, preferably between 100 to 150 degrees Celsius, where the resin viscosity and RPM of the centrifugal mixer yield well mixed particles with no visual agglomerates on the order of minutes.

The particle filled BMPN resin and resin blends offer advantages over previous phthalonitrile resins in terms of material properties and cost. For example, calcite filled phthalonitrile polymerized networks have greater stiffness and, in some examples, higher glass transition temperature or slightly higher toughness, while maintaining comparable strength. Silica filled phthalonitrile polymerized networks have greater stiffness and toughness while maintaining comparable strength. Alumina and boron nitride phthalonitrile polymerized networks have greater stiffness and thermal conductivity. Glass bubble filled phthalonitrile polymerized networks have greater stiffness and lower density.

The particle filled BMPN phthalonitrile resin and resin blends are processable as a liquid melt at temperatures below 200 degrees Celsius. When a dianiline based curative (e.g. 4,4'-(1,3-phenylenedioxy)dianiline) was added to the filled resin, the filled resin system had a viscosity and a working time before resin gelation that was controlled by the processing temperature. Upon heating the filled resin with curative to temperatures near and in excess of 200 degrees Celsius, the phthalonitrile readily polymerized into a networked polymer solid. The liquid-like viscosity and working time of the filled resin allowed the resin to be molded into particle filled polymer network articles and fiber reinforced polymer composite articles.

The manufacture of fiber reinforced polymer fibrous composite articles from a filled resin is enabled by the characteristic size of a particle filler mapped to a sphere being less than 1 micrometer, more preferably less than 400 nanometers, as is demonstrated, for instance, for milled calcite and solution dispersed silica and silicon carbide filled phthalonitrile resins. The manufacture of a fiber reinforced polymer composite was demonstrated by resin transfer molding of a calcite filled BMPN based resin system and an unfilled BMPN based resin system.

Compositions according to at least certain embodiments of the disclosure include one or more curatives. Such curatives often include an amine compound, such as a primary amine, for instance including an aniline functional residue. Combinations of various curatives can be used if desired. The curative is typically present in an amount of at least 1 percent by weight of the resin blend, at least 2 percent, at least 5 percent, at least 10 percent, at least 15 percent or even at least 20 percent by weight of the resin blend; and up to 40 percent by weight of the resin blend, up to 35 percent, up to 30 percent, or even up to 25 percent by weight of the resin blend; such as between 0 and 40 percent by weight of the resin blend. Higher molecular weight and lower volatility aniline functional curatives are typically desired to avoid loss of the curative during polymerization. Dianiline based curatives can be of value due to a higher aniline functionality per weight of the curative. Example dianiline based curatives that will promote phthalonitrile polymerization include for instance and without limitation, 4,4'-(1,3-phenylenedioxy)dianiline, 4,4'-(1,4-phenylenedioxy)dianiline, bis[4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis(p-phenyleneoxy)dianiline, and 4,4'-diaminobenzophenone. The primary amine promoted phthalonitrile cure reaction proceeds at an appreciable rate between temperatures of 200° C. to 250° C. Amine cured phthalonitrile polymerized networks have demonstrated excellent thermal stability imparted by a high glass transition temperature, good thermal and thermoxidative degradation resistance, plus are inherently non-flammable, and have low moisture uptake.

Certain other optional additives may also be included in compositions, two component systems, and/or resin blends according to the present disclosure, including, for example, tougheners, fillers, and combinations thereof. Such additives provide various functions. For instance, a toughening agent such as organic particles, may add strength to the composition after curing without interfering with curing. It will be understood by one of skill in the art that one compound may form two or more different functions. For example, a compound may function as both a toughening agent and a filler. In some embodiments, such additives will not react with the resins of the resin blend. In some embodiments, such additives may include reactive functional groups, particularly as end groups. Examples of such reactive functional groups include, but are not limited to, amines, thiols, alcohols, epoxides, vinyls, and combinations thereof.

Useful toughening agents are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski). Exemplary rubbery backbones include polymerized butadiene or a polymerized mixture of butadiene and styrene. Exemplary shells including polymerized methacrylic acid esters are lower alkyl (C1-C4) substituted methacrylates. Exemplary monovinyl aromatic hydrocarbons are styrene, alpha-methylstyrene, vinyltoluene, vinylxylene, ethylvinylbenzene, isopropylstyrene, chlorostyrene, dichlorostyrene, and ethyl-chlorostyrene. It is important that the graft copolymer contain no functional groups that would interfere with the polymerization of the resin.

Examples of useful toughening agents of the second type are acrylate core-shell graft copolymers wherein the core or backbone is a polyacrylate polymer having a glass transition temperature below 0° C., such as polybutyl acrylate or polyisooctyl acrylate to which is grafted a polymethacrylate polymer (shell) having a glass transition above 25° C., such as polymethylmethacrylate.

The third class of useful toughening agents includes elastomeric particles that have a glass transition temperature ($T_g$) below 25° C. before mixing with the other components of the composition. These elastomeric particles are polymerized from free radical polymerizable monomers and a copolymerizable polymeric stabilizer. The free radical polymerizable monomers are ethylenically unsaturated monomers or diisocyanates combined with co-reactive difunctional hydrogen compounds such as diols, diamines, and alkanolamines.

Useful toughening agents include core/shell polymers, such as methacrylate-butadiene-styrene (MBS) copolymer wherein the core is crosslinked styrene/butadiene rubber and the shell is polymethylacrylate (for example, those available under the trade names ACRYLOID KM653 and KM680, from Rohm and Haas, Philadelphia, Pa.), those having a core including polybutadiene and a shell including poly(methyl methacrylate) (for example, those available under the trade names KANE ACE M511, M521, B11A, B22, B31, and M901 from Kaneka Corporation, Houston, Tex. and CLEARSTRENGTH C223 from ATOFINA, Philadelphia, Pa.), those having a polysiloxane core and a polyacrylate shell (for example, those available under the trade names CLEARSTRENGTH S-2001 from ATOFINA and GENIOPERL P22 from Wacker-Chemie GmbH, Wacker Silicones, Munich, Germany), those having a polyacrylate core and a poly(methyl methacrylate) shell (for example, those available under the trade names PARALOID EXL2330 from Rohm and Haas and STAPHYLOID AC3355 and AC3395 from Takeda Chemical Company, Osaka, Japan), those having an MBS core and a poly(methyl methacrylate) shell (for example, those available under the trade names PARALOID EXL2691A, EXL2691, and EXL2655 from Rohm and Haas); and the like; and mixtures thereof.

As used above, for acrylic core/shell materials "core" will be understood to be an acrylic polymer having a $T_g$ of less than 0° C. and "shell" will be understood to be an acrylic polymer having a $T_g$ of greater than 25° C.

Other useful toughening agents include: carboxylated and amine terminated acrylonitrile/butadiene vulcanizable elastomer precursors, such as those available under the trade names HYCAR CTBN 1300X8, ATBN 1300X16, and HYCAR 1072 from B. F. Goodrich Chemical Co.; butadiene polymers, such as those available under the trade name HYCAR CTB; amine functional polyethers such as HCl 101 (i.e., polytetramethylene oxide diamine) a 10,000 MW, primary amine-terminated, compound from 3M Co., St. Paul, Minn., and those available under the trade name JEFFAMINE from Huntsman Chemical Co., Houston, Tex. Useful liquid polybutadiene hydroxyl terminated resins include those available under the trade names LIQUIFLEX H by Petroflex of Wilmington, Del., and HT 45 by Sartomer of Exton, PN.

Tougheners may include epoxy-terminated compounds, which can be incorporated into the polymer backbone. A typical, preferred, list of tougheners includes: acrylic core/shell polymers; styrene-butadiene/methacrylate core/shell polymers; polyether polymers; carboxylated acrylonitrile/butadienes; and carboxylated butadienes. Advantages can be obtained from the provision of the chain extension agent in a composition with an epoxy resin even in the absence of a toughening agent as described above. However, particular advantage is achieved from the presence of the toughening agent or combinations of different agents, as previously suggested.

Various combinations of toughening agents can be used if desired. If used, a toughening agent is present in the resin blend in an amount of at least 3 percent by weight, or at least 5 percent by weight. If used, a toughening agent is present in a resin blend in an amount of no greater than 35 percent by weight, or no greater than 25 weight percent.

Other optional additives, or adjuvants, may be added to the compositions as desired. Examples of such other optional additives include as colorants, anti-oxidant stabilizers, thermal degradation stabilizers, light stabilizers, flow agents, bodying agents, flattening agents, additional fillers, binders, blowing agents, fungicides, bactericides, surfactants, plasticizers, rubber tougheners, and other additives known to those skilled in the art. Such additives are typically substantially unreactive. These adjuvants, if present, or other optional additives, are added in an amount effective for their intended purpose.

Examples of additional suitable filler materials include reinforcement-grade carbon black, fluoroplastics, clays, and any combination of any of these in any proportions.

The phrase "reinforcement-grade carbon black" as used herein, includes any carbon black with an average particle size smaller than about 10 microns. Some particularly suitable average particle sizes for reinforcement-grade carbon black range from about 9 nm to about 40 nm. Carbon black that is not reinforcement grade include carbon black with an average particle size larger than about 40 nm. Carbon nanotubes are also useful fillers. Carbon black fillers are typically employed as a means to balance, elongation, hardness, abrasion resistance, conductivity, and processibility of compositions. Suitable examples include MT blacks (medium thermal black) designated N-991, N-990, N-908, and N-907; FEF N-550; and large particle size furnace blacks.

Further useful fillers include diatomaceous earth, barium sulfate, talc, and calcium fluoride. The choice and amounts of optional components depend on the needs of the specific application.

Various embodiments are provided that include resin blends and articles.

Embodiment 1 is resin blend comprising a blend of a first phthalonitrile resin, a filler, and a bisphenol M diphthalonitrile ether resin.

Embodiment 2 is the resin blend of embodiment 1, wherein the filler includes a nanofiller including metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof.

Embodiment 3 is the resin blend of embodiment 1 or embodiment 2, wherein the filler includes a nanofiller comprising calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof.

Embodiment 4 is the resin blend of any of embodiments 1 to 3, wherein the filler includes a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof.

Embodiment 5 is the resin blend of any of embodiments 1 to 4, wherein the filler includes a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof.

Embodiment 6 is the resin blend of any of embodiments 1 to 5, wherein the filler includes a surface modifier comprising an organoacid, an organobase, a siloxane, a silane, or a combination thereof, the surface modifier bonded to or associated with, or both, a surface of the filler.

Embodiment 7 is the resin blend of embodiment 6, wherein the filler includes silica nanoparticles, silica microparticles, cenospheres, zirconia nanoparticles, zirconia microparticles, magnesium oxide nanoparticles, magnesium oxide microparticles, silicon carbide nanoparticles, silicon carbide microparticles, or a combination thereof; and wherein the surface modifier comprises a silane or a siloxane.

Embodiment 8 is the resin blend of embodiment 6 or embodiment 7, wherein the filler includes calcite nanoparticles, calcite microparticles, magnesium oxide nanoparticles, magnesium oxide microparticles, alumina nanoparticles, alumina microparticles, dolomite nanoparticles, dolomite microparticles, boehmite nanoparticles, boehmite microparticles, or a combination thereof; and wherein the surface modifier comprises an organoacid or an organobase.

Embodiment 9 is the resin blend of embodiment 8, wherein the filler includes calcite nanoparticles, calcite microparticles, or a combination thereof; and wherein the surface modifier comprises an organosulfonate, an organophosphate, or a combination thereof.

Embodiment 10 is the resin blend of any of embodiments 6 to 8, wherein the filler includes zirconia nanoparticles, zirconia microparticles, magnesium oxide nanoparticles, magnesium oxide microparticles, or a combination thereof; and wherein the surface modifier comprises an organoacid.

Embodiment 11 is the resin blend of any of embodiments 1 to 10, including a nanofiller in an amount of 40 weight percent or less, based on the total weight of the resin blend.

Embodiment 12 is the resin blend of embodiment 11, including a nanofiller in an amount of 1 weight percent or more, based on the total weight of the resin blend.

Embodiment 13 is the resin blend of any of embodiments 1 to 10, including a microfiller in an amount of 90 weight percent or less, based on the total weight of the resin blend.

Embodiment 14 is the resin blend of embodiment 13, including a microfiller in an amount of 1 weight percent or more, based on the total weight of the resin blend.

Embodiment 15 is the resin blend of any of embodiments 1 to 14, further including at least one additive selected from a catalyst, a curative, a toughening agent, and combinations thereof.

Embodiment 16 is the resin blend of embodiment 15, wherein the curative includes a primary amine.

Embodiment 17 is the resin blend of embodiment 16, wherein the primary amine curative includes an aniline functional residue.

Embodiment 18 is the resin blend of any of embodiments 15 to 17, wherein the curative is present in an amount of 0 to 40 weight percent, based on the total weight of the resin blend.

Embodiment 19 is the resin blend of any of embodiments 1 to 18, wherein the bisphenol M diphthalonitrile ether resin is of Formula I:

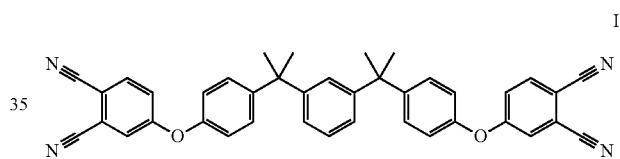

Embodiment 20 is the resin blend of any of embodiments 1 to 19, wherein the first phthalonitrile resin is of Formula II, Formula III, Formula IV, or a combination thereof:

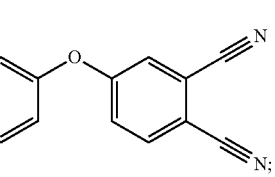

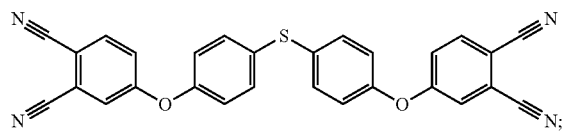

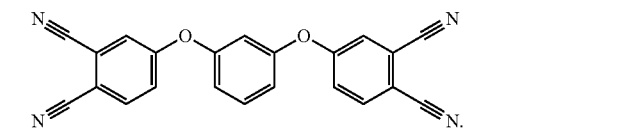

Embodiment 21 is the resin blend of embodiment 20, wherein the first phthalonitrile resin comprises a bisphenol P diphthalonitrile ether resin of Formula II.

Embodiment 22 is the resin blend of embodiment 20 or embodiment 21, wherein the first phthalonitrile resin comprises a bisphenol T diphthalonitrile ether resin of Formula III.

Embodiment 23 is the resin blend of any of embodiments 20 to 22, wherein the first phthalonitrile resin comprises a resorcinol diphthalonitrile ether resin of Formula IV.

Embodiment 24 is the resin blend of any of embodiments 1 to 23, wherein a weight ratio of the first phthalonitrile resin to the bisphenol M diphthalonitrile ether resin ranges from 10:90 to 90:10, inclusive.

Embodiment 25 is the resin blend of any of embodiments 1 to 24, wherein a weight ratio of the first phthalonitrile resin to the bisphenol M diphthalonitrile ether resin ranges from 15:85 to 85:15, inclusive.

Embodiment 26 is the resin blend of any of embodiments 1 to 25, wherein a weight ratio of the first phthalonitrile resin to the bisphenol M diphthalonitrile ether resin ranges from 30:70 to 70:30, inclusive.

Embodiment 27 is the resin blend of any of embodiments 1 to 26, wherein the filler includes at least one of reinforcing continuous fibers or reinforcing discontinuous fibers.

Embodiment 28 is an article comprising a polymerization product of the resin blend of any of embodiments 1 to 27.

Embodiment 29 is the article of embodiment 28, wherein the article exhibits a glass transition temperature between 200 and 350 degrees Celsius.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, hr=hour, kg=kilograms, min=minutes, mol=mole; cm=centimeter, mm=millimeter, nm=nanometer, mL=milliliter, L=liter, MPa=megaPascals, and wt.=weight.

Materials

| Name | Description |
| --- | --- |
| BMPN | Bisphenol M diphthalonitrile (i.e. bis(3,4-dicyanophenyl) ether of bisphenol M); prepared as described in Preparatory Example A of U.S. patent application No. 62/316,248 filed on 31 Mar. 2016 |
| RPN | Resorcinol diphthalonitrile (i.e. bis(3,4-dicyanophenyl) ether of resorcinol); prepared as described in Preparatory Example B of U.S. patent application No. 62/316,248 filed on 31 Mar. 2016 |
| BTPN | Bisphenol T diphthalonitrile (i.e. bis(3,4-dicyanophenyl) ether of bisphenol T); prepared as described in Preparatory Example C of U.S. patent application No. 62/316,248 filed on 31 Mar. 2016 |
| APPN | Allylphenol phthalonitrile (i.e. 4-(2-allylphenoxy)phthalonitrile); prepared as described below |
| APB | 4,4'-(1,3-phenyleneoxy)aniline; Sigma-Aldrich, St. Louis, MO |
| ALBAFIL | Calcium carbonate particulate; Specialty Minerals Inc., Bethlehem, PA |
| PS-nanosilica | Phenyl silane surface treated silica nanoparticle suspension in a mixture water/1-methoxy-2-propanol (27 wt. % silica); prepared as described below |
| PS-nano silicon carbide | Phenyl silane surface treated silicon carbide nanoparticle suspension in a mixture of water/1-methoxy-2-propanol (7 wt. % silicon carbide); prepared as described below |
| JAS | JEFFAMINE sulfonate; prepared according to the teachings of U.S. patent Pub. No. 2011-0245376 from JEFFAMINE M-600 and 1,3-Propanesultone |
| BYK-W 9012 | Phosphoric acid polyester dispersant; BYK USA Inc., Wallingford, CT |
| Boron Nitride | Boron Nitrile (BN) agglomerates; available from 3M Company, St. Paul, MN under trade designation "3M BORON NITRIDE COOLING FILLER PLATELETS" |
| Glass Bubbles | Glass Bubbles; commercially available from 3M Company, St. Paul, MN under trade designation "3M GLASS BUBBLES IM16K" |
| Alumina | Micron TA6Y1 alumina; Micron Corp, a subsidiary of the Nippon Steel and Sumikin Materials Co, Japan |
| NALCO 15827 | Silica obtained from Nalco Company, Naperville, IL |
| VSN1393 | Silicon carbide available from 3M Technical Ceramics, Kempten, Germany |
| JEFFAMINE M-600 | Polyetheramine from Huntsman, The Woodlands, Texas |
| DMSO (dimethyl sulfoxide) | obtained from Sigma Aldrich Chemical Company, St. Louis, MO |
| MTBE (metyl tert-butyl ether) | |
| MIBK (methyl isobutyl ketone) | |
| THF (tetrahydrofuran) | |
| trimethoxyphenylsilane | |
| 1-methoxy-2-propanol | |
| 4-nitrophthalonitrile | |
| 2-allylphenol | |
| bisphenol M | |
| $K_2CO_3$ | |
| 4,4'-(1,3-phenyleneoxy)aniline | |
| Acetone | |
| 1,3-Propanesultone | |

Methods
Method for Preparing APPN

APPN, allylphenol phthalonitrile (i.e. 4-(2-allylphenoxy) phthalonitrile) was derived from the nucleophilic substitution reaction of 4-nitrophthalonitrile and 2-allylphenol. To a three necked 1000 mL reaction flask was added 50 g (0.289 mol) of 4-nitrophthalonitrile, 38.75 g (0.289 mol) of 2-allylphenol, 79.83 g (0.578 mol) of anhydrous $K_2CO_3$, and 300 g of dry DMSO) and stirred for 48 hours at room temperature under a nitrogen atmosphere. The reaction solution was filtered through a Buchner funnel with Whatman #4 filter paper to remove undissolved salts. 300 mL of MTBE was added to the filtered reaction liquid followed by 300 mL of DI water. The addition of water induced phase separation of a top organic phase and a bottom aqueous phase. The bottom aqueous phase was separated in a 2 L separatory funnel. The organic phase was extracted with three subsequent 150 mL additions of DI water each followed by separation of the bottom aqueous phase. The organic phase was poured out of the top of the separatory funnel into a 1000 mL round bottom flask. The MTBE was stripped off of the organic phase on a BUCHI ROTAVAPOR R-215 rotary evaporator (from BUCHI Rotavapor, New Castle, Del. under trade designation "BUCHI ROTAVAPOR R-215") leaving a light tan viscous liquid. The liquid was collected and dried in a convection oven set at 120° C. The resin crystallized upon cooling. The product, 61.02 g (81.2%), had a melt temperature of 65° C., and was identified as the desired compound by infrared analysis.

Method for Preparing PS-Nanosilica 249.5 kg of NALCO 15827 was added to a kettle with stirring. A premix of 2.105 kg of trimethoxyphenylsilane in 203.2 kg of 1-methoxy-2-propanol was pumped into the kettle containing the NALCO 15827 and mixed for 30 minutes. The solution was pumped into a hot tube reactor as described in U.S. Pat. No. 8,394,977 with a reaction temperature of 149° C. and pressure of 20.4 atmospheres (2.07 MPa). Mixture was held at 149° C. for 35 minutes, then cooled to ambient temperature. The measured solids content by TGA was 24 wt. % of PS-nanosilica.

Method for Preparing PS-Nano Silicon Carbide 276 g of a 20.5 wt. % aqueous solution of VSN1393 silicon carbide was placed in a flask equipped with condenser, stirrer, thermo-watch and thermometer. While stirring at ambient temperature, a premix of 250 g of 1-methoxy-2-propanol and 0.405 g of trimethoxyphenylsilane was added slowly to the flask over a period of 5 minutes. The flask solution was heated to a temperature range of 90–95° C. The temperature of the flask solution was held at 90-95° C. for 20 hours. The flask solution was allowed to cool. The measured solids content by TGA was 6.0 wt. % PS-nanosilicon carbide.

Method of Measuring Particle Concentration

A 20 to 50 milligram sample of particle filled phthalonitrile (PN) resin or polymer network was placed in a TA Instruments Model TGA 500 thermogravimetric analyzer (obtained from TA Instruments, New Castle, Del.). The sample temperature was ramped up in air at 30° C. per minute from 50° C. to 900° C., and then held at 900° C. for 3 minutes. The residual weight is the particle weight of the sample and recorded as a weight percent concentration. For the specific case of calcite particles, the residual weight was assumed to be the CaO remaining in the sample after volatilizing all organics and carbon dioxide from the nanocalcite (e.g., calcite nanoparticles). The nanocalcite concentration in the original sample was calculated by dividing the weight percent CaO residue by 0.56.

Method of Measuring the Complex Shear Viscosity

A TA instruments Discovery Series HR-2 stress controlled rheometer with parallel plate geometry (obtained from TA Instruments, New Castle, Del.) was used to measure the complex shear viscosity. The tooling utilized an upper 40 mm top plate and a lower temperature controlled peltier plate. The gap between the upper and lower plate was 0.5 mm. The viscosity was measured by applying a 1% strain oscillation at a frequency of 1 Hz for 6 seconds, broken into a 3 second conditioning step and a 3 second measurement step.

Method of Measuring the Dynamic Modulus and the Glass to Rubber Transition Temperature Via a Dynamic Mechanical Analyzer (DMA)

A TA Instruments Q Series DMA (obtained from TA Instruments, New Castle, Del.) was used to measure low strain linear viscoelastic properties. Dynamic mechanical measurements were performed using single cantilever beam geometry. The low strain in-phase and out-of-phase deformation response was measured when applying a continuous oscillatory force with a controlled deformation amplitude of 20 micrometers at a frequency of 1 Hz, and the resulting storage and loss moduli and loss tangent were calculated ramping the temperature during the measurement. The temperature was ramped at 3° C./min over a temperature range spanning the glass to rubber transition. The glass transition temperature is characterized by the storage modulus (E') onset temperature.

Method of Performing Tensile Test

Specimen dimensions and measurement method followed ASTM D638-14 "Standard Test Method for Tensile Properties of Plastics". Six type 1 specimens with a thickness of 0.125" (3.18 mm) were loaded and the displacement was measured to break failure. Mean property measurements and standard deviation error limits were calculated based on specimen dimensions and load versus displacement measurements. Specimens were tested on a MTS Sintech 10/D load frame (obtained from MTS, Eden Prairie, Minn.) with a traceable calibration.

Method of Performing Compact Tension Test

Specimen dimensions and measurement method followed ASTM D5045 "Standard Test Method for Plane-Strain Fracture Toughness and Strain Energy Release Rate of Plastic Materials". Six square like specimens with dimensions of 1.25"×1.20"×0.25" (3.18 cm×3.05 cm×1.27 cm) were notched and pre-cracked according to the test specification. $K_{1C}$ measurements were calculated from the measured $P_Q$ load in a continuous loading experiment to initiate crack propagation. Specimens were tested on a MTS Sintech 10/D load frame (obtained from MTS, Eden Prairie, Minn.) with a traceable calibration.

Method of Measuring the Thermal Conductivity:

A low speed diamond saw was used to cut disc-shaped specimens measuring 2.0 mm thick and 12.5 mm in diameter from a cylindrical shaped starting material. Each disc specimen was measured for density using Archimedes Method of water displacement. The specimens were spray coated with DGF-123 dry graphite film lubricant (obtained from Miracle Power Products Corporation, Cleveland, Ohio, under trade designation "DGF-123 DRY GRAPHITE FILM LUBRICANT") until they were black and opaque. Along with the sample specimens, a reference sample of CORNING PYROCERAM—GLASS CODE 9606 (Corning Incorporated, Corning, N.Y., under trade designation "CORNING PYROCERAM—GLASS CODE 9606") was sprayed and included in the measurement to serve as system control and the reference specimen for heat capacity measurement.

Thermal diffusivity and specific heat capacity were measured using a LFA 467 HYPERFLASH—Light Flash Apparatus (from Netzsch Instruments North America, LLC, Burlington, Mass.) according to ASTM E1461-13 "Standard Test Method for Thermal Diffusivity by the Flash Method." For a given sample, three specimens were evaluated by collecting five thermograms at each temperature point for thermal diffusivity and heat capacity calculations. The results of the three specimens were used to calculate and report an average value. Thermal conductivity (k) for each specimen was calculated as the product of the average sample thermal diffusivity (a (alpha)), specific heat capacity ($C_P$), and density (r (rho)) (i.e.: k=a*Cr*r). Standard deviation of a specimen thermal conductivity was calculated by propagation of component standard deviations.

Comparative Example A 288 g of BMPN, RPN and BTPN in a 4/1/1 mass ratio were melted and mixed at a temperature of 190° C. in a flat bottom aluminum pan. The phthalonitrile resin blend was cooled to 100° C. The resin blend remained in a liquid state. The complex shear viscosity of the PN resin blend of Comparative Example A as a function of temperature between 100 and 200° C. is shown in FIG. 1.

12 g of 4,4'-(1,3-phenyleneoxy)aniline was added to the resin blend and stirred into the resin at 135° C. The final composition (weight fraction) of the phthalonitrile resin system was 0.96 of the phthalonitrile resin blend and 0.04 of the 4,4'-(1,3-phenyleneoxy)aniline curative. The resin system was poured into plaque molds with thickness of 0.0625 inches (0.16 cm), 0.125 inches (0.32 cm) and 0.25 inches (0.64 cm) preheated to a temperature of 160° C. The resin filled plaque molds were placed in an air circulating oven set at 200° C. and cured for 5 hours. The resin system underwent a thermosetting network polymerization to a hard stiff solid. After 5 hours, the plaques were cooled at 5° C./min to 40° C. The PN cured plaques were removed from the molds and subjected to a free standing post cure at 300° C. for 24 hours. After 24 hours, the plaques were cooled at 5° C./min to 40° C. The plaques were cut into test specimens for mechanical testing using the methods described above. The mechanical properties of Comparative Example A samples are summarized in Table 1, below.

Figure 2:
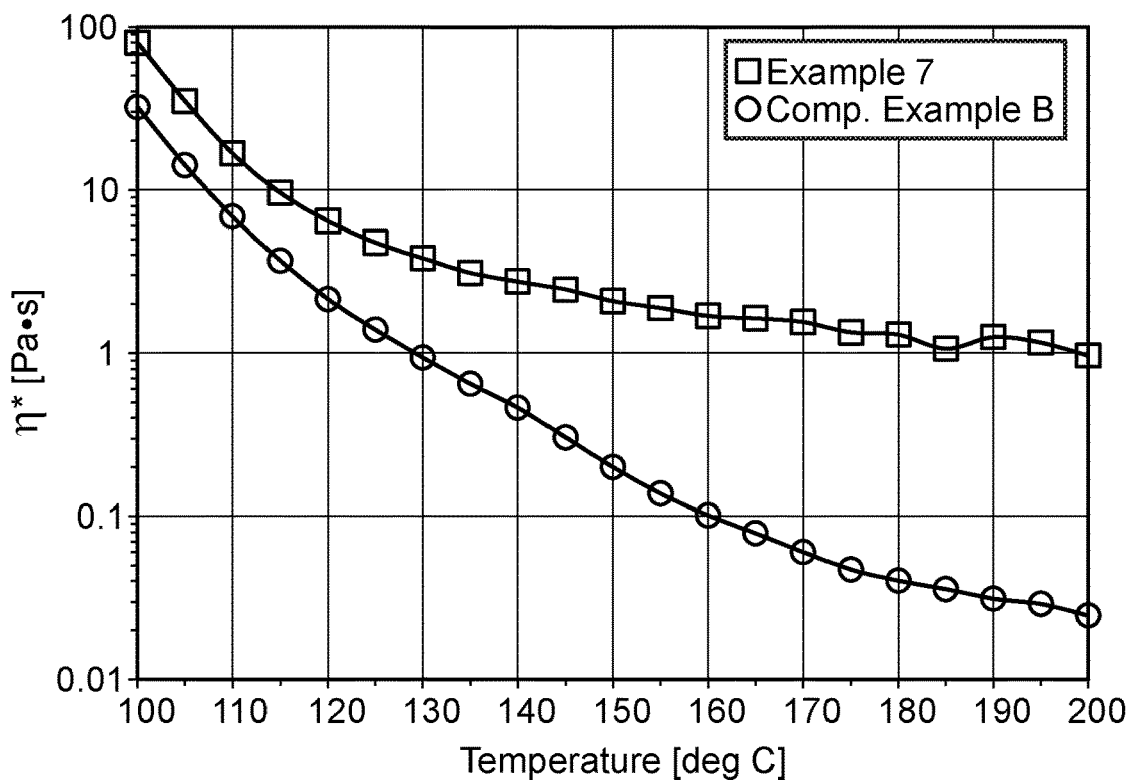
FIG. 2 is a graph of complex shear viscosity as a function of temperature of the filled resin blends of Example 7 (squares) and Comparative Example B (circles).

FIG. 2 shows an SEM image of the compact tension fracture surface of the unfilled cured PN system of Comparative Example A.

Example 1

The 300 g of a PN resin blend (4:1:1 parts by weight of BMPN, RPN, BTPN, respectively) was weighed into a stainless steel beaker and 300 g of MIBK was added. The PN resin blend in MIBK was heated to 100° C. to assist dissolution of the resin in MIBK. The PN/MIBK solution was cooled to ambient temperature. 15.0 g of JAS and 300 g of ALBAFIL (in 3 separate 100 g additions) were added to the PN/MIBK solution. The JAS and ALBAFIL were blended into the PN/MIBK solution by agitation with a Cowles blade. The slurry was agitated for 1 hour before transferring to the double-walled stainless-steel milling vessel (preheated at 55° C. bath temperature) connected to a thermostated circulating bath (ISOTEMP 6200 R20, from Fisher Scientific, Pittsburgh, Pa.)

Milling was performed with a Hockmeyer Immersion Micromill (Hockmeyer, Harrison, N.J.) fitted with a 0.25 mm separation screen, and loaded with 155 g of 0.5 mm yttrium-stabilized zirconia beads. The milling was ran for 2 hours starting at 3000 RPM in the first 30 minutes then ramping to 3500 RPM until the end of milling. An additional 50 g of MIBK was added during the milling process (40 g after the first 30 minutes, 10 g after 1 hour and 30 minutes). The nanocalcite concentration was determined to be 31.08 wt. % using the Method of Measuring Particle Concentration described above. The resulting sample had a particle size distribution with mean particle size of 238 nm, a standard deviation of 49 nm and D90 of 303 nm, as determined according to the Calcite Particle Size Procedure described in paragraph [0047] of US Application Publication No. 2011/0245376 (Schultz et al.).

The milled material was stripped of MIBK using a BUCHI ROTAVAPOR R-215 (obtained from BUCHI Rotavapor, New Castle, Del., under trade designation "BUCHI ROTAVAPOR R-215"). The bath temperature started at 80° C. and was slowly raised to 150° C. until the removal of solvent ceased. A light green crumbly powder was obtained (approximate 51 wt. % JAS-nanocalcite in PN resin). The flow temperature of the filled resin was determined to be around 170° C. The filled resin was then diluted to 38 wt. % JAS-nanocalcite by the addition of neat PN resin blend. The mixture was heated to 170° C. and agitated with a 3-blade impeller in a stainless steel beaker. A final drying step was performed in a vacuum oven set at 200° C. for 1 hour at 1 Torr (133.3 Pa) to remove any residual solvent. The melt viscosity of the 38 wt. % JAS-nanocalcite/PN resin was measured between 100 to 200° C. The nanocalcite concentration was determined to be 36.0 wt. % by thermogravimetric analysis. The complex shear viscosity of the JAS-nanocalcite/PN resin of Example 1 as a function of temperature is shown in FIG. 1 and compared to that of PN resin of Comparative Example A.

Example 2

400 g of JAS-nanocalcite filled BMPN, RPN and BTPN resin blend from Example 1 was heated to a temperature of 150° C. in a flat bottom aluminum pan. 10.4 g of 4,4'-(1,3-phenyleneoxy)aniline was added to the resin blend and stirred into the resin. The 4,4'-(1,3-phenyleneoxy)aniline was added at a weight fraction of 0.04 compared to the PN resin blend portion of the JAS-nanocalcite filled PN resin blend. After melting and blending of the 4,4'-(1,3-phenyleneoxy)aniline into the resin, the resin system was degassed at 135° C. to remove entrapped air. The final composition (weight fraction) of the JAS-nanocalcite filled PN resin system was 0.351 nanocalcite, 0.018 JAS, 0.606 of PN resin blend and 0.025 of the 4,4'-(1,3-phenyleneoxy)aniline curative. The resin system was poured into plaque molds with thickness of 0.0625 inches (0.16 cm), 0.125 inches (0.32 cm) and 0.25 inches (0.64 cm) preheated to a temperature of 160° C. The resin filled plaque molds were placed in an air circulating oven set at 200° C. and cured for 5 hours. The resin system underwent a thermosetting network polymerization to a hard stiff solid. After 5 hours, the plaques were cooled at 5° C./min to 40° C. The plaques were removed from the molds and subjected to a free standing post cure at 300° C. for 24 hours. After 24 hours, the plaques were cooled at 5° C./min to 40° C. The plaques were cut into test specimens for mechanical testing using the methods described above. The mechanical properties of Example 2 samples are summarized in Table 1, below.

Example 3

579.9 g of a PN resin blend (4:1:1 parts by weight of BMPN, RPN, BTPN, respectively) was weighed into the double-walled stainless steel milling vessel connected to a thermostated circulation bath (Model Polystat 3007 100 CS, from Cole Parmer, Court Vernon Hills, Ill.) filled with silicone oil (210H Fluid, from BOSS Products, Elizabethtown, Ky.). The bath temperature was set at 160° C. The resin melted to a low viscosity liquid with a measured temperature of 155° C. 23.8 g BYK-W 9012 and 870 g of ALBAFIL (in 1 addition of 500 g and 1 addition of 370 g) was added to the PN resin blend. The BYK-W 9012 and ALBAFIL were blended into the PN resin blend by agitation with a Cowles blade. The slurry was agitated for one hour. The filled liquid resin was degassed at 150° C. to remove entrapped air introduced during the milling process. The microcalcite concentration was determined to be 45.3 wt. % by thermogravimetric analysis. The complex shear viscosity at 120° C. was measured to be 8.8 Pa·s.

Example 4

20 g of BYK-W 9012-microcalcite filled BMPN, RPN and BTPN resin blend from Example 3 was heated to a temperature of 150° C. in a flat bottom aluminum pan. 0.438 g of 4,4'-(1,3-phenyleneoxy)aniline was added to the resin blend and stirred into the resin. The 4,4'-(1,3-phenyleneoxy) aniline was added at a weight fraction of 0.04 compared to the PN resin blend portion of the BYK-W 9012-microcalcite filled PN resin blend. After melting and blending of the 4,4'-(1,3-phenyleneoxy)aniline into the resin, the resin system was degassed at 135° C. to remove entrapped air. The final composition (weight fraction) of the microcalcite filled PN resin system was 0.443 nanocalcite, 0.021 BYK-W 9012, 0.515 of PN resin blend and 0.021 of the 4,4'-(1,3-phenyleneoxy)aniline curative. The resin system was heated to 160° C. and poured into a plaque mold with thickness of 0.0625 inches (0.16 cm) preheated to a temperature of 160° C. The resin filled plaque mold were placed in an air circulating oven set at 200° C. and cured for 5 hours. The resin system underwent a thermosetting network polymerization to a hard stiff solid. After 5 hours, the plaque was cooled at 5° C./min to 40° C. The plaque was removed from the molds and subjected to a free standing post cure at 300° C. for 24 hours. After 24 hours, the plaque was cooled at 5° C./min to 40° C. The plaque was cut into test specimens for mechanical testing using the methods described above. The storage modulus, E' at 25° C. was measured to be 4.8 GPa, and the storage modulus onset temperature, E'(onset) was measured to be 254° C.

Example 5

1194 g of a 43.16 wt. % BYK-W 9012-microcalcite dispersion in a PN resin blend (4:1:1 parts by weight of BMPN, RPN, BTPN, respectively) was weighed into the double-walled stainless steel milling vessel connected to a thermostated circulation bath (Model Polystat 3007 100 CS, from Cole Parmer, Court Vernon Hills, Ill.) filled with silicone oil (210H Fluid, from BOSS Products, Elizabethtown, Ky.). The bath temperature was set at 160° C. The BYK-W 9012-microcalcite dispersion was milled using Hockmeyer Immersion Micromill (Hockmeyer, Harrison, N.J., USA) fitted with a 0.25 mm separation screen, and loaded with 155 g of 0.5 mm yttrium-stabilized zirconia beads. The milling was performed for 3 hours starting at 2500 RPM for the first 30 minutes and increased to 3000 RPM until the end of milling. The filled liquid resin was degassed at 150° C. to remove entrapped air introduced during the milling process. The nanocalcite concentration was determined to be 41.2 wt. % by thermogravimetric analysis. The resulting sample had a particle size distribution with mean particle size of 340 nm, a standard deviation of 204 nm and D90 of 481 nm, as determined according to the Calcite Particle Size Procedure described in paragraph [0047] of US Application Publication No. 2011/0245376 (Schultz et al.). The complex shear viscosity of the BYK-W 9012-nanocalcite/PN resin of Example 5 as a function of temperature is shown in FIG. 1 and compared to that of the PN resin of Comparative Example A.

Example 6

450 g of BYK-W 9012-nanocalcite filled BMPN, RPN and BTPN resin blend from Example 5 was heated to a temperature of 150° C. in a flat bottom aluminum pan. 11.8 g of 4,4'-(1,3-phenyleneoxy)aniline was added to the resin blend and stirred into the resin. The 4,4'-(1,3-phenyleneoxy) aniline was added at a weight fraction of 0.04 compared to the PN resin blend portion of the nanocalcite-BYK-W 9012 filled PN resin blend. After melting and blending of the 4,4'-(1,3-phenyleneoxy)aniline into the resin, the resin system was degassed at 135° C. to remove entrapped air. The final composition (weight fraction) of the nanocalcite filled PN resin system was 0.400 nanocalcite, 0.020 BYK-W 9012, 0.555 of PN resin blend and 0.025 of the 4,4'-(1,3-phenyleneoxy)aniline curative. The resin system was heated to 160° C. and poured into plaque molds with thickness of 0.0625 inches (0.16 cm), 0.125 inches (0.32 cm) and 0.25 inches (0.64 cm) preheated to a temperature of 160° C. The resin filled plaque molds were placed in an air circulating oven and cured for 5 hours at 200° C. The resin system underwent a thermosetting network polymerization to a hard stiff solid. After 5 hours, the plaques were cooled at 5° C./min to 40° C. The plaques were removed from the molds and subjected to a free standing post cure at 300° C. for 24 hours. After 24 hours, the plaques were cooled at 5° C./min to 40° C. The plaques were cut into test specimens for mechanical testing using the methods described above. Specimen dimensions and testing procedure is presented under test methods. The mechanical properties of Example 6 samples are summarized in Table 1, below.

Figure 3:
FIG. 3 is a scanning electron microscope (SEM) image of a surface of the Comparative Example A filled polymer network, following a compact tension test.

FIG. 3 shows an SEM image of the compact tension fracture surface of the nanocalcite filled cured PN system of Example 6.

Comparative Example B 288 g of BMPN and RPN in a 2/1 mass ratio were melted and mixed at a temperature of 190° C. in a flat bottom aluminum pan. The phthalonitrile resin blend was cooled to 100° C. The resin blend remained in a liquid state. The complex shear viscosity of the PN resin blend of Comparative Example B as a function of temperature between 100 to 200° C. is shown in FIG. 2.

12 g of 4,4'-(1,3-phenyleneoxy)aniline was added to the resin blend and stirred into the resin at 135° C. The final weight composition of the phthalonitrile resin system was 0.96 of the phthalonitrile resin blend and 0.04 of the 4,4'-(1,3-phenyleneoxy)aniline curative. The resin system was poured into plaque molds with thickness of 0.0625 inches (0.16 cm), 0.125 inches (0.32 cm) and 0.25 inches (0.64 cm) preheated to a temperature of 160° C. The resin filled plaque molds were placed in an air circulating oven set at 200° C. and cured for 5 hours. The resin system underwent a thermosetting network polymerization to a hard stiff solid. After 5 hours, the plaques were cooled at 5° C./min to 40°

C. The PN cured plaques were removed from the molds and subjected to a free standing post cure at 300° C. for 24 hours. After 24 hours, the plaques were cooled at 5° C./min to 40° C. The plaques were cut into test specimens for mechanical testing using the methods described above. The mechanical properties of Comparative Example B samples are summarized in Table 1, below.

Example 7

200 g of PS-nanosilica suspension in water/1-methoxy-2-propanol was stripped of water using a BUCHI ROTAVAPOR R-215 with back additions of 1-methoxy-2-propanol. The final solution was 51.5 wt. % PS-nanosilica in 1-methoxy-2-propanol. 265 g of a BMPN based resin blend (2:1 parts by weight of BMPN and RPN, respectively) was dissolved in 1185 g of THF/Acetone (30/70). 1423 g of the PN resin blend in THF/Acetone was added to 275 g of the PS-nanosilica in 1-methoxy-2-propanol and solvent stripped on a BUCHI ROTAVAPOR R-215 with an initial bath temperature of 100° C. and increased over time to 125° C. until the majority of the solvent had been removed. A final strip was performed at 180° C. to remove residual solvent. The PS-nanosilica filled PN resin was removed from the roto-evaporator flask while still hot. The resin was finally degassed in a vacuum oven at 185° C. until foam-rise-collapse. The nanosilica concentration was determined to be 36.5 wt. % by thermogravimetric analysis. The complex shear viscosity of the PS-nanosilica/PN resin of Example 7 as a function of temperature is shown in FIG. 2 and compared to the PN resin blend of Comparative Example B.

Example 8

400 g of PS-nanosilica filled PN resin blend from Example 7 was heated to a temperature of 150° C. in a flat bottom aluminum pan. 10.6 g of 4,4'-(1,3-phenyleneoxy) aniline was added to the resin blend and stirred into the resin. The 4,4'-(1,3-phenyleneoxy)aniline was added at a weight fraction of 0.04 compared to the PN resin blend portion of the phenyl-nanosilica/PN resin. After melting and blending of the 4,4'-(1,3-phenyleneoxy)aniline into the resin, the resin system was degassed at 150° C. in a vacuum oven to remove entrapped air. The final composition (weight fraction) of the PS-nanosilica/PN resin system was 0.356 PS-nanosilica, 0.619 of PN resin blend and 0.025 of the 4,4'-(1,3-phenyleneoxy)aniline curative. The resin system was heated to 175° C. and poured into plaque molds with thickness of 0.0625 inches (0.16 cm), 0.125 inches (0.32 cm) and 0.25 inches (0.64 cm) preheated to a temperature of 175° C. The resin filled plaque molds were placed in an air circulating oven set at 200° C. and cured for 5 hours. The resin system underwent a thermosetting network polymerization to a hard stiff solid. After 5 hours, the plaques were cooled at 5° C./min to 40° C. The plaques were removed from the molds and subjected to a free standing post cure at 300° C. for 24 hours. After 24 hours, the plaques were cooled at 5° C./min to 40° C. The plaques were cut into test specimens for mechanical testing using the methods described above. The mechanical properties of Example 8 samples are summarized in Table 1, below.

Figure 4:
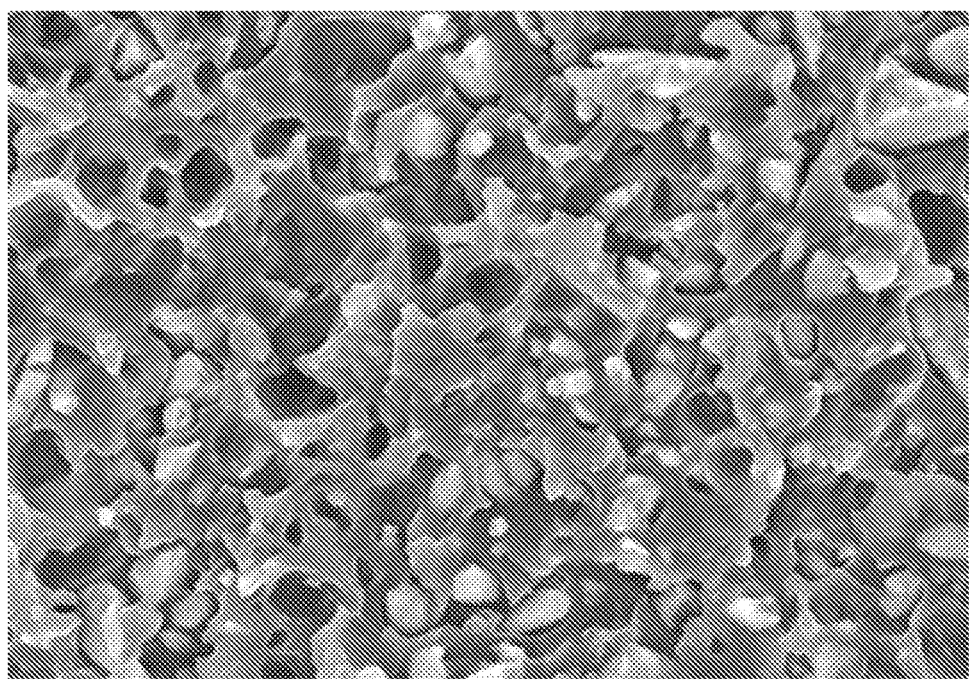
FIG. 4 is a scanning electron microscope (SEM) image of a surface of the Example 6 filled polymer network, following a compact tension test.
Figure 5:
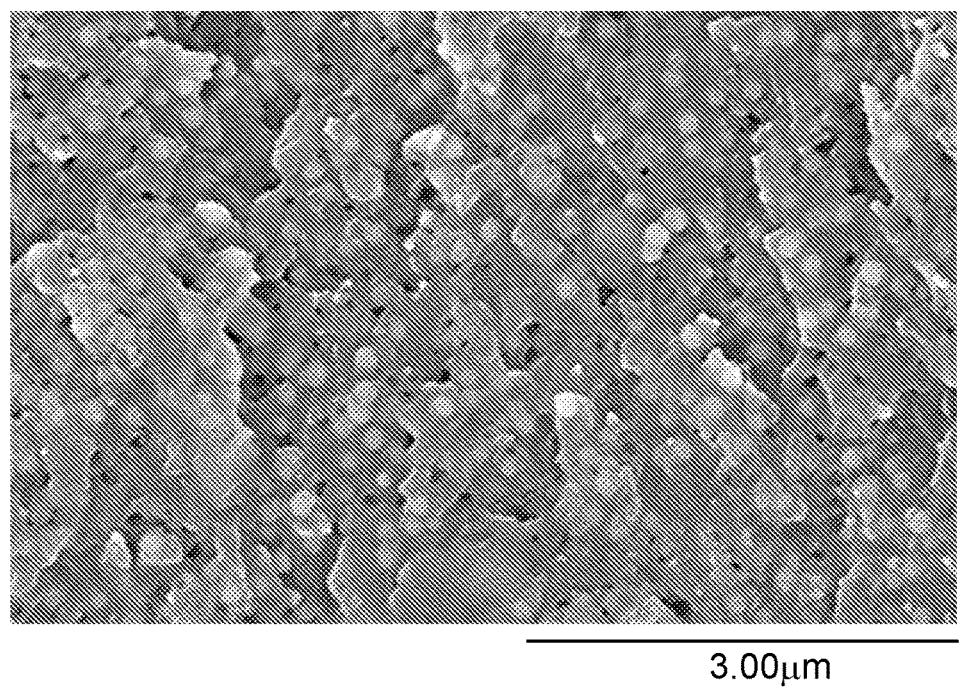
FIG. 5 is a scanning electron microscope (SEM) image of a surface of the Example 8 filled polymer network, following a compact tension test.

FIG. 4 shows an SEM image of the compact tension fracture surface of the nanosilica filled cured PN system of Example 8.

TABLE 1

| Example | $T_g$ (E' onset, °C.) | Stiffness (GPa) | Tensile Ultimate Strength (MPa) | Tensile Ultimate Strain (%) | $K_{1C}$ (MPa·m$^{1/2}$) |
|---|---|---|---|---|---|
| Comp. Ex. A | 240 | 3.4 | 80 ± 6 | 3.0 ± 0.2 | 0.72 |
| Example 2 | 262 | 6.2 | 72 ± 2 | 1.3 ± 0.1 | 0.71 |
| Example 6 | 240 | 5.8 | 71 ± 9 | 1.3 ± 0.1 | 0.76 |
| Comp. Ex. B | 278 | 3.4 | 78 ± 7 | 3.0 ± 0.5 | 0.58 |
| Example 8 | 278 | 5.1 | 76 ± 6 | 1.5 ± 0.2 | 1.14 |

Example 9

200 g of PS-nanosilica suspension in water/1-methoxy-2-propanol was air dried in a foil pan to a powder at room temperature. Powder was placed in acetone at approximately 30 wt. % solids and high shear mixed using a SILVERSON mixer (from Silverson Machines Inc., East Longmeadow, Mass.) until fully dispersed. The PS suspension in acetone was poured through a 53 micrometer nylon mesh to remove any large chunks (none were visibly apparent). The suspension was measured to be 29.1 wt. % PS-nanosilica in acetone.

31.6 g of a BMPN based resin blend (4:1:1 parts by weight of BMPN, RPN, BTPN, respectively) was dissolved in 168.4 g of MIBK. 73 g of the PN resin blend in MIBK was added to 26.4 g of the PS-nanosilica in acetone and solvent stripped on a BUCHI ROTAVAPOR R-215 with an initial bath temperature of 65° C. and increased over time to 160° C. until the majority of the solvent had been removed. The resin was removed from the roto-evaporator flask while still hot. A final strip and degassing was performed in a vacuum oven at 185° C. to remove residual solvent and entrapped air. The nanosilica concentration was determined to be 40.7 wt. % by thermogravimetric analysis. The complex shear viscosity of the PS-nanosilica/PN resin of Example 8 as a function of temperature is shown in FIG. 1 and compared to the PN resin of Comparative Example A.

Example 10

200 g of PS-nanosilica suspension in water/1-methoxy-2-propanol was stripped of water using a BUCHI ROTAVAPOR R-215 with back additions of 1-methoxy-2-propanol. The final solution was 50.4 wt. % PS-nanosilica in 1-methoxy-2-propanol. 31.6 g of a BMPN based resin blend (4:1:1 parts by weight of BMPN, RPN, BTPN, respectively) was dissolved in 168.4 g of MIBK. 73 g of the PN resin blend in MIBK preheated to 70° C. was added to 15.2 g of the PS-nanosilica in 1-methoxy-2-propanol also preheated to 70° C. Solvent was stripped from the PS-nanosilica/PN resin solution on a BUCHI ROTAVAPOR R-215 with an initial bath temperature of 100° C. and increased over time to 160° C. until the majority of the solvent had been removed. The resin was removed from the roto-evaporator flask while still hot. A final strip and degassing was performed in a vacuum oven at 185° C. to remove residual solvent and entrapped air. The nanosilica concentration was determined to be 41.2 wt. % by thermogravimetric analysis.

Example 11

400 g of the PS-nanosilicon carbide suspension in water/1-methoxy-2-propanol (6 wt. % silicon carbide) was air dried to a free flowing powder in a foil pan at room temperature. Powder was placed in acetone at approximately 30 wt. % solids and high shear mixed using a SILVERSON mixer until fully dispersed. The PS-nanosilicon carbide suspension in acetone was poured through a 100 micrometer nylon mesh to remove any large chunks. The suspension was measured to be 28.5 wt. % PS-nanosilicon carbide in acetone by thermogravimetric analysis.

50 g of a BMPN based resin blend (2:1 parts by weight of BMPN and RPN, respectively) was dissolved in 325 g of THF. The PN resin solids concentration was measured at 13.4 wt. % in THF. 304 g of the PN resin blend in THF was added to 81 g of the PS-nanosilicon carbide in acetone and solvent stripped on a BUCHI ROTAVAPOR R-215 with an initial bath temperature of 95° C. to remove the majority of volatiles. The temperature of the oil bath was increased to 150° C. for 10 min followed by 165° C. for 30 min. The resin was removed from the roto-evaporator flask while still hot. The PS-nanosilicon carbide concentration was determined to be 34.8 wt. % by thermogravimetric analysis.

Example 12

40 g of Micron TA6Y1 alumina was dispersed into 20 g of BMPN based resin blend (4:2:3 parts by weight of BMPN, RPN, APPN, respectively) using a Speedmixer (Model DAC 400 KLV, from FlackTek Inc., Landrum, S.C. under trade designation "SPEEDMIXER DAC 400 KLV") with 4,4'-(1,3-phenyleneoxy)aniline curative added at 4 wt. % of the PN resin blend preheated to 130° C. The alumina and PN resin system were mixed for 5 minutes at 2750 RPM. The mixture was a low viscosity liquid after the alumina addition. Four subsequent additions of 20 g of alumina followed by preheating to 130° C. and mixing for 5 minutes at 2750 RPM brought the total weight of material to 140 g and a final weight fraction of 0.857 of alumina in the filled resin. The viscosity of the filled resin had increased but would flow freely when heated to 120° C. The viscosity of the resin was measured to be 2.3 Pa·s. A small vial was filled with the alumina/resin mixture and placed in an oven set at 125° C. There was no clear sign of visual settling as the mixture sat in the oven at 125° C. for 1 hour. The filled resin system was cured by heating for 3 hours at 175° C., 5 hours at 200° C., and 24 hours at 300° C. The stiffness of the filled polymer network was measured by dynamic mechanical analysis using single cantilever beam geometry to be 14.8 GPa at 25° C., and the storage modulus onset temperature, E'(onset) was measured to be 310° C. The thermal conductivity was measured to be 2.4+/−0.2 W/m·K.

Example 13

5 g of boron nitride agglomerate platelets were dispersed into 30 g of BMPN based resin blend (4:2:3 parts by weight of BMPN, RPN, APPN, respectively) using a DAC 400 KLV Speedmixer with 4,4'-(1,3-phenyleneoxy)aniline curative added at 4 wt. % of the PN resin blend preheated to 130° C. The boron nitride and PN resin system were mixed for 5 minutes at 2750 RPM. The mixture was a low viscosity liquid after the boron nitride addition. Three subsequent additions of 20 g of boron nitride followed by preheating to 130° C. and mixing for 5 minutes at 2750 RPM brought the total weight of material to 50 g and a final weight fraction of 0.4 of boron nitride in the filled resin. The viscosity of the filled resin had increased but would flow freely when heated to 120° C. The viscosity of the resin was measured to be 2.5 Pa·s. The filled resin system was cured by heating for 3 hours at 175° C., 5 hours at 200° C., and 24 hours at 300° C. The stiffness of the filled polymer network was measured by dynamic mechanical analysis using single cantilever beam geometry to be 5.0 GPa at 25° C., and the storage modulus onset temperature, E'(onset) was measured to be 295° C.

Example 14

Example 14 was run in the same manner as Example 13, except for an initial addition of 5 g and two subsequent additions of 20 g iM16K glass bubbles instead of an initial addition of 5 g and three subsequent additions of 20 g boron nitride agglomerates. The final weight fraction of iM16K glass bubbles in the filled resin was 0.3. The viscosity of the resin was measured to be 3.0 Pa·s. The stiffness of the filled polymer network was measured by dynamic mechanical analysis using single cantilever beam geometry to be 3.6 GPa at 25° C., and the storage modulus onset temperature, E'(onset) was measured to be 320° C.

Example 15

Example 15 was run in the same manner as Example 14 except that iM16K glass bubbles were replaced with APS-iM16K glass bubbles. The viscosity of the resin was measured to be 1.9 Pa·s. The stiffness of the filled polymer network was measured by dynamic mechanical analysis using single cantilever beam geometry to be 3.5 GPa at 25° C., and the storage modulus onset temperature, E'(onset) was measured to be 320° C.

Example 16

400 g of BMPN, RPN and BTPN in a 4/1/1 mass ratio was blended with 16.67 g of 4,4'-(1,3-phenyleneoxy)aniline curative at 135° C. with stirring and allowed to cool to ambient temperature. The BMPN based resin blend system was added to the injector cylinder of a 2100 cc Series® injector (from Radius Engineering, Inc., South Salt Lake, Utah). The solid resin was melted in the injector cylinder at 140° C. and degassed under vacuum (less than 0.1 Torr (13.3 Pa)) using an air mixer head for agitation. Fourteen layers of a 5 harness satin weave fabric of 6K HEXTOW IM7 CARBON FIBER (form Hexcel Corp., Stamford, Conn., under trade designation "HEXTOW IM7 CARBON FIBER"), stacked in a symmetric quasi-isotropic layup configuration was placed in a closed metal mold. The internal dimensions of the two-part mold were 330 mm by 330 mm by 4 mm. The mold was held in a hot press with approximately 180 kN of clamping force (approximately 870 kPa clamping pressure). The mold was evacuated to less than 0.1 Torr (13.3 Pa) of absolute pressure and pre-heated to an injection temperature of 160° C. The injection was conducted with the injector cylinder heated to 140° C., a heated line from the injector cylinder to the mold heated to 140° C., and a mold temperature of 160° C. Vacuum of less than 0.1 Torr (13.3 Pa) was applied during the mold filling process. When resin was detected at the mold exit, the exit valve was closed. Resin was injected up to a pressure of 100 psi (690 kPa). The panel was cured for approximately 15 hours at 205° C. The panel was demolded and post-cured for 24 hours in an air convection oven set at 300° C. The panel showed good overall quality with low porosity. Based on fabric properties and the measured panel thickness, the fiber volume fraction was estimated to be 67%.

Figure 6:
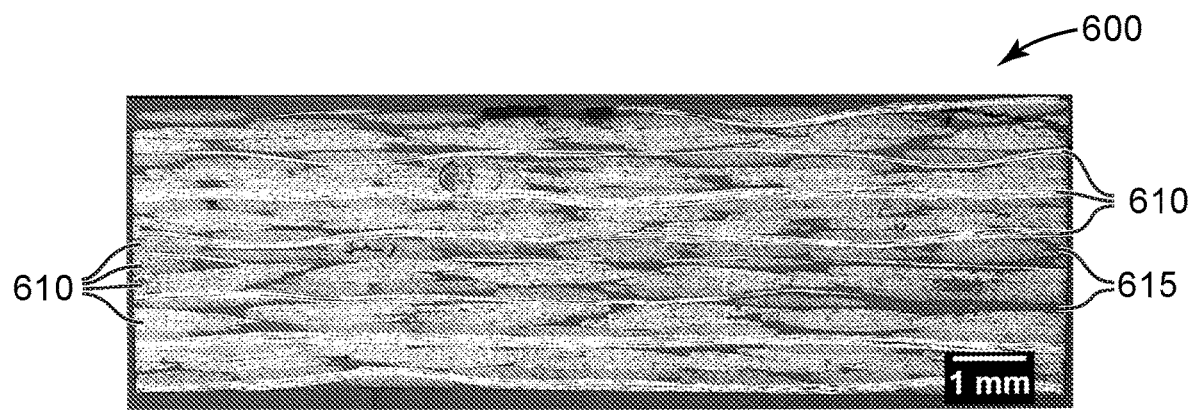
FIG. 6 is an optical microscope image of a cured composite panel of Example 16.

FIG. 6 is an optical microscope image of a cured composite panel 600 of Example 16, including a plurality of fibers 610 and resin matrix 615.

Example 17

130 g of BYK-W 9012-nanocalcite filled BMPN based resin of Example 5 was melt blended with 300 g of additional BMPN, RPN and BTPN blend resin in a 4/1/1 mass ratio at 160° C. The resin was cooled to 135° C. and was blended with 15.58 g of 4,4'-(1,3-phenyleneoxy)aniline curative with stirring and allowed to cool to ambient temperature. The mass fraction of nanocalcite was calculated to be 0.12. The BYK-W 9012-nanocalcite filled BMPN based resin was added to the injector cylinder of a 2100 cc Series® injector. The solid resin was melted in the injector cylinder at 140° C. and degassed under vacuum (less than 0.1 Torr (13.3 Pa)) using an air mixer head for agitation. Seven layers of a HexForce SGP196-P plain weave fabric (197 g/m2, 6K Hexcel IM7GP carbon fiber), stacked in a [0]$_7$ layup configuration, was placed in a closed metal mold. The internal dimensions of the two-part mold were 330 mm by 330 mm by 1.4 mm. The mold was held in a hot press with 180 kN of clamping force (approximately 870 kPa clamping pressure). The mold was evacuated to less than 0.1 Torr (13.3 Pa) of absolute pressure and pre-heated to an injection temperature of 160° C. The injection was conducted with the injector cylinder heated to 140° C., a heated line from the injector cylinder to the mold heated to 140° C., and a mold temperature of 160° C. Vacuum of less than 0.1 Torr (13.3 Pa) was applied during the mold filling process. When resin was detected at the mold exit, the exit valve was closed. Resin was injected up to a pressure of 100 psi (690 kPa). The panel was cured for 6 hours at 205° C. The panel was demolded and post-cured for 24 hours in an oven set at 300° C. The panel showed good overall quality with low porosity. Based on fabric properties and the measured panel thickness, the fiber volume fraction was estimated to be 57%.

Figure 7:
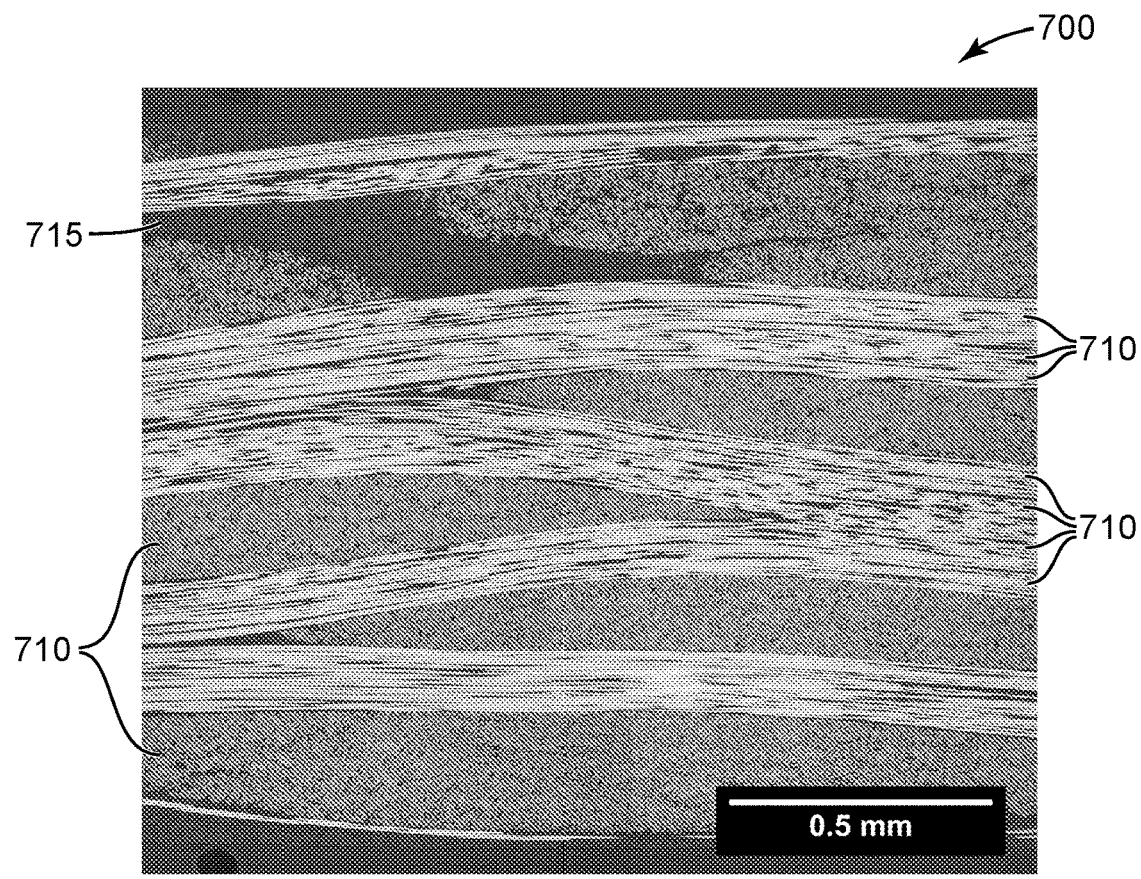
FIG. 7 is an optical microscope image of a polished cross-section of a cured composite panel of Example 17.
Figure 8:
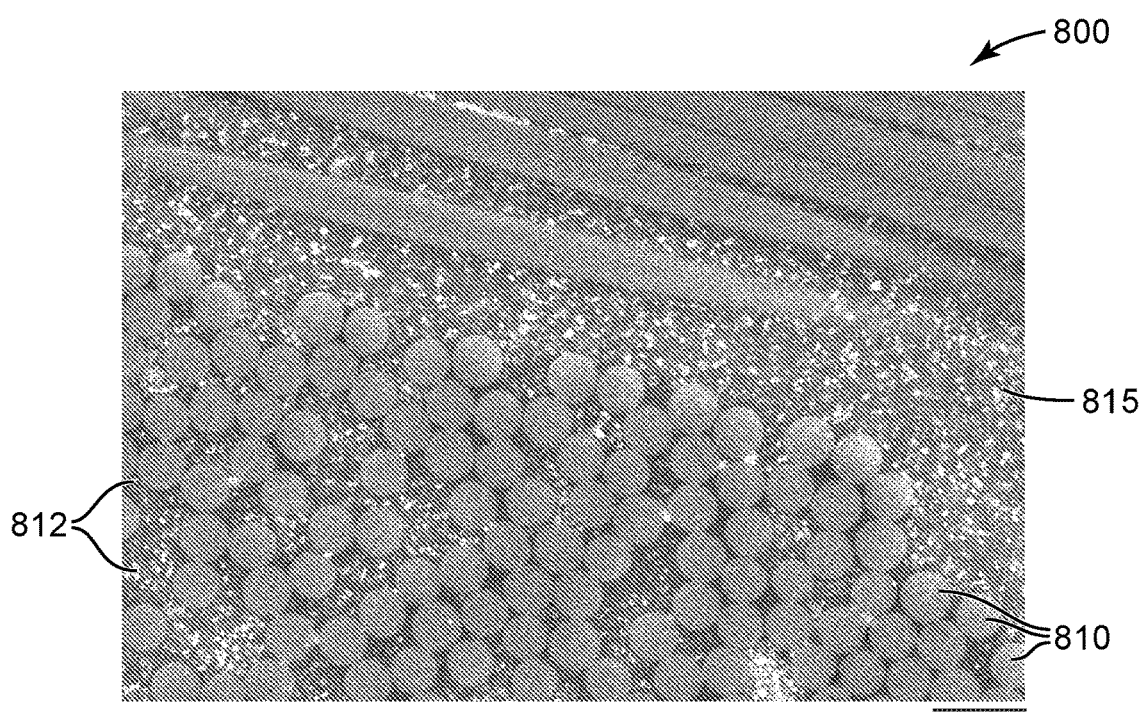
FIG. 8 is a scanning electron microscope (SEM) image of a polished cross-section of a composite panel of Example 17.

FIG. 7 is an optical microscope image of a polished cross-section of a cured composite panel 700 of Example 17, including a plurality of fibers 710 and nanocalcite filled resin matrix 715. FIG. 8 is a scanning electron microscope (SEM) image of a polished cross-section of the composite panel 800 of FIG. 7, including a plurality of fibers 810 and nanocalcite filled resin matrix 815. Calcite nanoparticles 812 can be seen at the high magnification of the SEM image.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A resin blend comprising a blend of a first phthalonitrile resin, a filler, and a bisphenol M diphthalonitrile ether resin.

2. The resin blend of claim 1, wherein the filler comprises a nanofiller comprising metal carbide nanoparticles, metal oxide nanoparticles, silica nanoparticles, carbon nanoparticles, metal carbonate nanoparticles, metal nitride nanoparticles, metal hydroxide nanoparticles, metal sulfate nanoparticles, barium titanate nanoparticles, or a combination thereof.

3. The resin blend of claim 1, wherein the filler comprises a nanofiller comprising calcite nanoparticles, silica nanoparticles, silicon carbide nanoparticles, alumina nanoparticles, zirconia nanoparticles, magnesium oxide nanoparticles, aluminum nitride nanoparticles, boron nitride nanoparticles, dolomite nanoparticles, boehmite nanoparticles, magnesium hydroxide nanoparticles, calcium sulfate nanoparticles, barium sulfate nanoparticles, magnesium sulfate nanoparticles, or a combination thereof.

4. The resin blend of claim 1, wherein the filler comprises a microfiller comprising metal carbide microparticles, metal oxide microparticles, silica microparticles, carbon microparticles, metal carbonate microparticles, metal nitride microparticles, metal hydroxide nanoparticles, metal sulfate microparticles, barium titanate microparticles, cenospheres, or a combination thereof.

5. The resin blend of claim 1, wherein the filler comprises a microfiller comprising calcite microparticles, silica microparticles, silicon carbide microparticles, alumina microparticles, magnesium oxide microparticles, aluminum nitride microparticles, boron nitride microparticles, dolomite microparticles, boehmite microparticles, glass bubbles, or a combination thereof.

6. The resin blend of claim 1, wherein the filler comprises a surface modifier comprising an organoacid, an organobase, a siloxane, a silane, or a combination thereof, the surface modifier bonded to or associated with, or both, a surface of the filler.

7. The resin blend of claim 6, wherein the filler comprises silica nanoparticles, silica microparticles, cenospheres, zirconia nanoparticles, zirconia microparticles, magnesium oxide nanoparticles, magnesium oxide microparticles, silicon carbide nanoparticles, silicon carbide microparticles, or a combination thereof and wherein the surface modifier comprises a silane or a siloxane.

8. The resin blend of claim 6, wherein the filler comprises calcite nanoparticles, calcite microparticles, magnesium oxide nanoparticles, magnesium oxide microparticles, alumina nanoparticles, alumina microparticles, dolomite nanoparticles, dolomite microparticles, boehmite nanoparticles, boehmite microparticles, or a combination thereof; and wherein the surface modifier comprises an organoacid or an organobase.

9. The resin blend of claim 8, wherein the filler comprises calcite nanoparticles, calcite microparticles, or a combination thereof and wherein the surface modifier comprises an organosulfonate, an organophosphate, or a combination thereof.

10. The resin blend of claim 6, wherein the filler comprises zirconia nanoparticles, zirconia microparticles, magnesium oxide nanoparticles, magnesium oxide microparticles, or a combination thereof and wherein the surface modifier comprises an organoacid.

11. The resin blend of claim 1, wherein the bisphenol M diphthalonitrile ether resin is of Formula I:

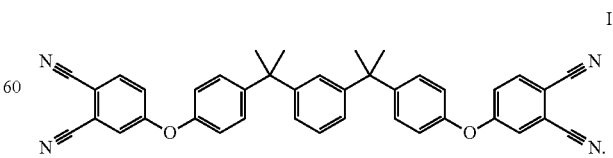

I

12. The resin blend of claim 1, wherein the first phthalonitrile resin is of Formula II, Formula III, Formula IV, or a combination thereof:

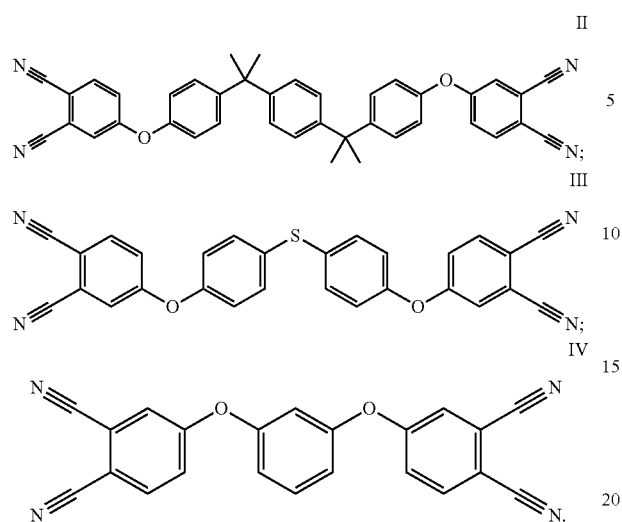
13. The resin blend of claim 1, wherein the filler comprises at least one of reinforcing continuous fibers or reinforcing discontinuous fibers.
14. An article comprising a polymerization product of the resin blend of claim 1.
15. The article of claim 14, wherein the article exhibits a glass transition temperature between 200 and 350 degrees Celsius.
* * * * *

UNITED STATES PATENT AND TRADEMARK OFFICE
CERTIFICATE OF CORRECTION

PATENT NO. : 10,899,865 B2  Page 1 of 1
APPLICATION NO. : 16/088876
DATED : January 26, 2021
INVENTOR(S) : Anderson et al.

It is certified that error appears in the above-identified patent and that said Letters Patent is hereby corrected as shown below:

In the Specification

Columns 19 & 20,
Lines 55-60, delete

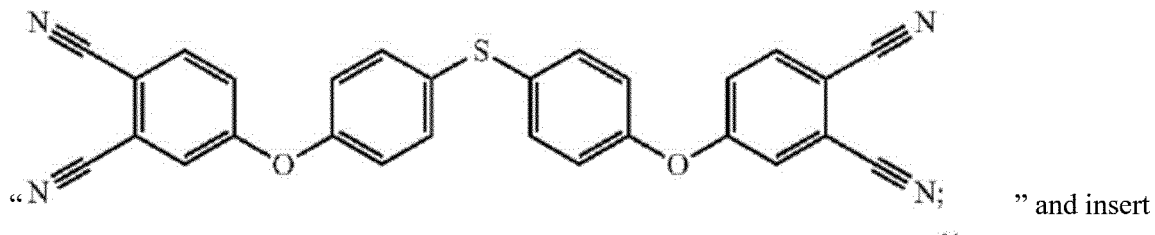 " and insert

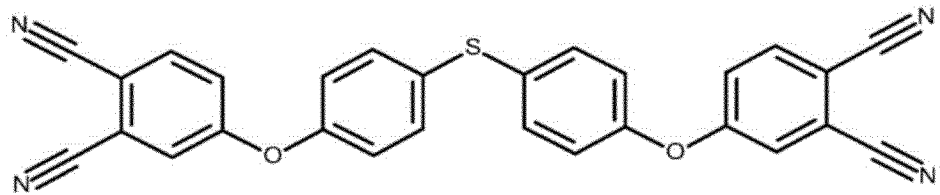 --, therefor.

Column 25,
Line 13, delete "a*Cr*r)." and insert -- $\alpha*C_P*r$). --, therefor.

In the Claims

Column 34,
Line 32, in Claim 7, delete "thereof" and insert -- thereof; --, therefor.
Line 45, in Claim 9, delete "thereof" and insert -- thereof; --, therefor.
Line 52, in Claim 10, delete "thereof" and insert -- thereof; --, therefor.

Signed and Sealed this
Second Day of March, 2021

Drew Hirshfeld
*Performing the Functions and Duties of the
Under Secretary of Commerce for Intellectual Property and
Director of the United States Patent and Trademark Office*